United States Patent [19]

Anderson et al.

[11] Patent Number: 5,279,960
[45] Date of Patent: Jan. 18, 1994

[54] **25 KD COCCIDIAL ANTIGEN OF *EIMERIA TENELLA***

[75] Inventors: David M. Anderson, Rockville; Russell J. McCandliss, Gaithersburg; Susan L. Strausberg; Robert L. Strausberg, both of Silver Spring; Michael D. Ruff, Bowie; Harry D. Danforth, Severn; Patricia C. Augustine, Laurel, all of Md.

[73] Assignees: Enzon Corp., Piscataway, N.J.; U.S.A. Dept. of Agriculture, Washington, D.C.

[21] Appl. No.: 879,137

[22] Filed: May 5, 1992

Related U.S. Application Data

[63] Continuation of Ser. No. 215,162, Jul. 5, 1988, abandoned, which is a continuation-in-part of Ser. No. 746,520, Jun. 19, 1985, abandoned, which is a continuation-in-part of Ser. No. 627,811, Jul. 5, 1984, abandoned.

[51] Int. Cl.[5] ............ A61K 39/012; C07K 15/04; C12N 15/30; C12N 15/67
[52] U.S. Cl. .................. 435/243; 530/822; 530/388.6; 435/69.3; 435/320.1; 935/12; 935/66; 424/88; 536/23.7
[58] Field of Search ......... 435/69.3, 69.6, 320.1, 435/243; 530/387, 822, 388.1, 388.2, 388.6; 935/15, 12; 424/88.8; 536/88, 23.7

[56] References Cited

U.S. PATENT DOCUMENTS

| | | | |
|---|---|---|---|
| 4,710,377 | 12/1987 | Schenkel et al. | 424/88 |
| 4,724,145 | 2/1988 | Murray et al. | |
| 4,874,705 | 10/1989 | Andrews et al. | 435/252.33 |

FOREIGN PATENT DOCUMENTS

| | | |
|---|---|---|
| 10135712 | 8/1983 | European Pat. Off. |
| 10135073 | 3/1985 | European Pat. Off. |
| 10164176 | 12/1985 | European Pat. Off. |
| 10167443 | 1/1986 | European Pat. Off. |
| 10231537 | 8/1987 | European Pat. Off. |
| 0291123 | 11/1988 | European Pat. Off. ... A61K 39/012 |
| 20337589 | 1/1989 | European Pat. Off. |
| 0324648 | 7/1989 | European Pat. Off. |
| 20324648 | 7/1989 | European Pat. Off. |
| 0344808 | 12/1989 | European Pat. Off. |
| 20344808 | 12/1989 | European Pat. Off. |

OTHER PUBLICATIONS

Danforth et al. Avian Diseases 30(1):37–42, Use of . . . Antibodies and Recomb. DNA Tech. in Vaccine Dev.
Proferis—Juchelka et al. Mol. & Biochem. Parasit. 30:233–242 (1988).
Wisher Mol. and Biochem. Para. 21:7–15 (1986) Id of sporozite antigens of *Eim. tenella*.
Broome et al. PNAS 75:2746–2749 (1978) Immunol. Screening Method.
Augustine et al., *Avian Diseases* 29(4):1212–1223 (1985).
Augustine et al., *Proc. Helminthol. Soc. Wash.* 54(2):207–211 (1987).
Augustine et al. *Molecular Strategies of Parasitic Invasion*, Alan R. Liss, Inc. pp. 511–520 (1987).
Augustine et al., *J. Parasit.* 74(4):653–659 (1988).
Danforth, *J. Parasitol.* 68(3):392–397 (1982).
Danforth et al., *Poultry Science* 62:2145–2151 (1983).
Danforth, *Am. J. Vet. Res.* 44(9):1722–1727 (1983).
Danforth et al., *Fed. Proc. 44:1334 #5398 (1985)*.

*Primary Examiner*—David L. Lacey
*Assistant Examiner*—T. Michael Nisbet
*Attorney, Agent, or Firm*—Sterne, Kessler, Goldstein & Fox

[57] ABSTRACT

A cloned gene or fragment thereof encodes antigenic proteins that bind with a monoclonal or polyvalent antibody that is directed against an antigenic protein of avian coccidia.

6 Claims, 15 Drawing Sheets

```
Leu Leu Leu Leu Leu Leu Leu Leu Leu Gln Gly Ala Glu Cys Leu Leu Arg Ser Ser Lys   20
CTG CTG CTG CTG CTG CTG CTG CTG CTG CAG GGC GCG GAG TGC CTC TTG AGG AGC AGC AAA   60

Leu Ala Leu Glu Ala Leu Leu Glu Gly Ala Arg Val Ala Ala Thr Arg Gly Leu Leu Leu   40
CTG GCC CTC GAG GCC CTC CTC GAG GGG GCC CGC GTT GCA GCA ACG CGG GGT TTG CTG CTG   120

Val Glu Ser Ser Lys Asp Thr Val Leu Arg Ser Ile Pro His Thr Gln Glu Lys Leu Ala   60
GTC GAG AGC AGC AAA GAC ACG GTG CTG CGC AGC ATT CCC CAC ACC CAG GAG AAG CTG GCT   180

Gln Ala Tyr Ser Ser Phe Leu Arg Gly Tyr Gln Gly Ala Ala Ala Gly Arg Ser Leu Gly   80
CAG GCC TAC AGT TCT TTC CTG CGG GGC TAC CAG GGG GCA GCA GCG GGG AGG TCT CTG GGC   240

Tyr Gly Ala Pro Ala Ala Ala Tyr Gly Gln Gln Gln Gln Pro Ser Ser Tyr Gly Ala Pro   100
TAC GGC GCC CCT GCT GCT GCT TAC GGC CAG CAG CAG CAG CCC AGC AGC TAC GGG GCG CCC   300

Pro Ala Ser Ser Gln Gln Pro Ser Gly Phe Phe Trp ***                               113
CCC GCC TCC AGC CAG CAG CCC TCC GGC TTC TTC TGG TAG                                339
```

FIG. 1

| Gly | Gln | Thr | Gly | Glu | Glu | Gly | Thr |
|-----|-----|-----|-----|-----|-----|-----|-----|
| GGC | CAA | ACC | GGA | GAG | GAG | GGA | ACG |
| Glu | Gly | Gly | Ala | Gly | Gly | Ala | Gly |
| GAG | GGA | GGC | GCA | GGC | GGT | GCT | GGA |
| Gly | Ser | Gly | Gly | Ala | Glu | Glu | Leu |
| GGA | TCC | GGT | GGT | GCT | GAG | GAG | CTG |
| Pro | Gly | Glu | Glu | Gly | Gly | Ala | Gly |
| CCC | GGA | GAA | GAG | GGT | GGC | GCA | GGT |
| Ala | Gly | Gly | Glu | Gly | Gly | Ser | Gly |
| GCC | GGC | GGA | GAA | GGA | GGC | TCT | GGC |
| Gly | Asn | Ala | Glu | Glu | Leu | Pro | Gly |
| GGT | AAT | GCT | GAG | GAG | CTG | CCC | GGA |
| Glu | Gly | Gly | Ala | Gly | Glu | Ala | Gly |
| GAA | GGG | GGT | GCT | GGC | GAA | GCT | GGA |
| Gly | Ser | Gly | Gly | Ser | Ala | Glu | Glu |
| GGC | TCT | GGC | GGT | AGT | GCT | GAG | GAG |
| Leu | Pro | Gly | Glu | Glu | Gly | Gly | Ala |
| CTG | CCC | GGA | GAA | GAG | GGC | GGC | GCA |
| Gly | Ala | Gly | Gly | Gly | Gly | Gly | Ser |
| GGT | GCC | GGC | GGA | GGA | GGA | GGC | TCT |
| Gly | Gly | Ser | Ala | Glu | Glu | Leu | Pro |
| GGC | GGT | AGT | GCT | GAG | GAG | CTG | CCT |
| Gly | Glu | Glu | Gly | Gly | Ala | Gly | Ala |
| GGA | GAA | GAG | GGC | GGC | GCA | GGT | GCC |
| Gly | Gly | Glu | Gly | Gly | Ser | Gly | Gly |
| GGC | GGA | GAA | GGA | GGC | TCT | GGC | GGC |
| Asn | Ala | Glu | Glu | Leu | Pro | Gly | Glu |
| AAT | GCT | GAG | GAG | CTG | CCC | GGA | GAA |
| Glu | Gly | Gly | Ala | Gly | Ala | Gly | Gly |
| GAG | GGC | GGC | GCA | GGT | GCT | GGA | GGA |
| Ala | Glu | Gly | Glu | Thr | Gly | Lys | Pro |
| GCC | GAA | GGC | GAG | ACA | GGG | AAA | CCT |
| Gly | Gly | Glu | Glu | Gly | Gly | Ala | Gly |
| GGC | GGC | GAA | GAG | GGT | GGC | GCA | GGC |
| Gly | Ala | Gly | Glu | Gly | Ala | Gly | Gly |
| GGC | GCT | GGT | GAG | GGT | GCT | GGC | GGT |
| Glu | Gly | Gly | Glu | Val | Gln | Pro | Gly |
| GAA | GGT | GGT | GAG | GTC | CAG | CCT | GGA |

FIG. IA

| Glu | Gly | Glu | Gly | Ala | Ser | Glu | Gly |
|---|---|---|---|---|---|---|---|
| GAG | GGA | GAA | GGG | GCG | AGT | GAA | GGA |
| Gly | Glu | Gln | Val | Pro | Glu | Thr | Pro |
| GGC | GAG | CAA | GTG | CCG | GAA | ACC | CCT |
| Glu | Thr | Pro | Glu | Pro | Glu | Thr | Pro |
| GAG | ACA | CCC | GAA | CCG | GAA | ACA | CCT |
| Glu | Ala | Glu | Arg | Pro | Glu | Glu | Gln |
| GAA | GCT | GAG | AGA | CCT | GAA | GAG | CAA |
| Pro | Ser | Thr | Glu | Thr | Pro | Ala | Glu |
| CCC | TCG | ACG | GAA | ACT | CCA | GCA | GAG |
| Glu | Pro | Thr | Glu | Gly | Gly | Ala | Glu |
| GAG | CCC | ACC | GAA | GGC | GGT | GCA | GAA |
| Glu | Glu | Glu | Lys | Glu | Glu | Gly | Ser |
| GAA | GAG | GAG | AAG | GAG | GAG | GGC | AGC |
| Gly | Phe | Pro | Thr | Ala | Ala | Val | Ala |
| GGC | TTC | CCC | ACG | GCA | GCT | GTT | GCC |
| Gly | Gly | Val | Gly | Gly | Val | Leu | Leu |
| GGA | GGT | GTA | GGT | GGT | GTA | CTA | CTG |
| Leu | Ala | Ala | Val | Gly | Gly | Gly | Val |
| CTG | GCA | GCA | GTG | GGT | GGT | GGC | GTT |
| Ala | Ala | Tyr | Ser | Gly | Gly | Gly | Gly |
| GCC | GCG | TAC | TCC | GGT | GGT | GGT | GGA |
| Gly | Gly | Gly | Ala | Glu | Glu | Ala | Glu |
| GGT | GGC | GGT | GCC | GAG | GAG | GCT | GAG |
| Gln | Val | Glu | Phe | Glu | Gly | Glu | Glu |
| CAA | GTT | GAG | TTT | GAA | GGT | GAA | GAG |
| Ser | Gly | Gly | Ala | Ser | Ala | Glu | Thr |
| TCG | GGT | GGT | GCG | TCT | GCC | GAA | ACA |
| Pro | Glu | Ala | Asp | Thr | Val | Ile | Asp |
| CCT | GAG | GCT | GAT | ACT | GTG | ATT | GAC |
| Ile | Thr | Asp | Glu | Asp | Asp | Tyr | Trp |
| ATC | ACT | GAC | GAA | GAC | GAC | TAC | TGG |
| Ala | Asp | Ser | Gly | Asp | Ile | Gln |  |
| GCA | GAC | AGT | GGT | GAC | ATC | CAG | TAG |

FIG. 2

```
                    Leu Pro Gly Glu Glu Gly Gly Ala Gly Ala Gly Gly Gly Gly Gly Ser
                    CTG CCC GGA GAA GAG GGC GGC GCA GGT GCC GGC GGA GGA GGA GGC TCT

Gly Gly Ser Ala Glu Glu Leu Pro Gly Glu Glu Gly Gly Ala Gly Ala Gly Gly Glu Gly
GGC GGT AGT GCT GAG GAG CTG CCT GGA GAA GAG GGC GGC GCA GGT GCC GGC GGA GAA GGA

Gly Ser Gly Gly Asn Ala Glu Glu Leu Pro Gly Glu Glu Gly Gly Ala Gly Ala Gly Gly
GGC TCT GGC GGC AAT GCT GAG GAG CTG CCC GGA GAA GAG GGC GGC GCA GGT GCT GGA GGA

Ala Glu Gly Glu Thr Gly Lys Pro Gly Gly Glu Glu Gly Gly Ala Gly Gly Ala Gly Glu
GCC GAA GGC GAG ACA GGG AAA CCT GGC GGC GAA GAG GGT GGC GCA GGC GGC GCT GGT GAG

Gly Ala Gly Gly Glu Gly Gly Glu Val Gln Pro Gly Glu Gly Glu Gly Ala Ser Glu Gly
GGT GCT GGC GGT GAA GGT GGT GAG GTC CAG CCT GGA GAG GGA GAA GGG GCG AGT GAA GGA

Gly Glu Gln Val Pro Glu Thr Pro Glu Thr Pro Glu Pro Glu Thr Pro Glu Ala Glu Arg
GGC GAG CAA GTG CCG GAA ACC CCT GAG ACA CCC GAA CCG GAA ACA CCT GAA GCT GAG AGA

Pro Glu Glu Gln Pro Ser Thr Glu Thr Pro Ala Glu Glu Pro Thr Glu Gly Gly Ala Glu
CCT GAA GAG CAA CCC TCG ACG GAA ACT CCA GCA GAG GAG CCC ACC GAA GGC GGT GCA GAA

Glu Glu Glu Lys Glu Glu Gly Ser Gly Phe Pro Thr Ala Ala Val Ala Gly Gly Val Gly
GAA GAG GAG AAG GAG GAG GGC AGC GGC TTC CCC ACG GCA GCT GTT GCC GGA GGT GTA GGT

Gly Val Leu Leu Leu Ala Ala Val Gly Gly Gly Val Ala Ala Tyr Ser Gly Gly Gly Gly
GGT GTA CTA CTG CTG GCA GCA GTG GGT GGT GGC GTT GCC GCG TAC TCC GGT GGT GGT GGA

Gly Gly Gly Ala Glu Glu Ala Glu Gln Val Glu Phe Glu Gly Glu Glu Ser Gly Gly Ala
GGT GGC GGT GCC GAG GAG GCT GAG CAA GTT GAG TTT GAA GGT GAA GAG TCG GGT GGT GCG

Ser Ala Glu Thr Pro Glu Ala Asp Thr Val Ile Asp Ile Thr Asp Glu Asp Asp Tyr Trp
TCT GCC GAA ACA CCT GAG GCT GAT ACT GTG ATT GAC ATC ACT GAC GAA GAC GAC TAC TGG

Ala Asp Ser Gly Asp Ile Gln ***
GCA GAC AGT GGT GAC ATC CAG TAG
```

FIG. 3

```
              5                      10                      15                      20
Glu Val Glu Thr Val Gln Lys Ser Pro Cys Pro Val Gln Gln Gln Pro Gly Pro Trp Ser
GAG GTT GAA ACG GTG CAG AAA TCG CCG TGC CCA GTT CAG CAA CAA CCG GGA CCC TGG AGT
                25                      30                      35                      40
Glu Trp Thr Glu Cys Ser Ala Thr Cys Gly Gly Gly Thr Lys His Arg Glu Arg Glu Gly
GAA TGG ACA GAG TGC TCA GCA ACC TGC GGA GGA GGT ACT AAG CAT CGC GAG CGA GAG GGT
                45                      50                      55                      60
Leu Pro Gln Glu Gly Glu Leu Tyr Gly Gly Gln Thr Leu Glu Gln Gln Gly Ile Ala Val
TTG CCA CAG GAA GGG GAA CTG TAC GGG GGA CAG ACT TTG GAA CAA CAA GGC ATT GCT GTG
                65                      70                      75                      80
Arg Glu Thr Ala Ser Cys Ser Glu Asn Pro Cys Pro Ile Asp Ala Thr Cys Gly Glu Trp
AGG GAA ACT GCT TCG TGC AGC GAG AAC CCG TGC CCT ATC GAC GCA ACG TGC GGA GAA TGG
                85                      90                      95                     100
Thr Glu Tyr Ser Ala Cys Ser Arg Thr Cys Gly Gly Gly Thr Gln Glu Arg Lys Arg Glu
ACA GAG TAC AGT GCG TGC TCC AGA ACT TGC GGA GGC GGT ACC CAA GAG AGG AAG AGG GAG
               105                     110                     115                     120
Pro Trp Leu Asp Asn Ala Gln His Gly Gly Arg Thr Cys Met Glu Gln Tyr Pro Asp Gly
CCG TGG TTG GAT AAT GCG CAA CAC GGG GGG CGC ACC TGC ATG GAA CAG TAT CCT GAT GGG
               125                     130                     135                     140
Pro Ile Ser Val Arg Glu Cys Asn Thr Gln Pro Cys Pro Val Asp Glu Val Val Gly Asp
CCC ATA TCG GTC AGG GAG TGC AAC ACC CAG CCG TGC CCT GTG GAC GAA GTA GTT GGT GAT
               145                     150                     155                     160
Trp Glu Asp Trp Gly Gln Cys Ser Glu Gln Cys Gly Gly Gly Lys Arg Thr Arg Asn Arg
TGG GAA GAC TGG GGG CAA TGC AGC GAA CAG TGT GGT GGC GGC AAG CGG ACT CGT AAT CGC
               165                     170                     175                     180
Gly Pro Ser Lys Gln Glu Ala Met Phe Gly Gly Lys Thr Val Ala Gln Gln Asn Ala Glu
GGC CCA AGC AAG CAA GAG GCC ATG TTC GGA GGC AAG ACA GTT GCT CAA CAG AAC GCA GAG
               185                     190                     195                     200
Leu Pro Glu Gly Glu Lys Ile Glu Val Val Gln Glu Glu Gly Cys Asn Glu Val Pro Cys
CTC CCT GAA GGC GAG AAG ATT GAG GTG GTT CAG GAA GAA GGA TGC AAT GAA GTT CCA TGC
               205                     210                     215                     220
Gly Pro Cys Thr Leu Pro Phe Ser Glu Trp Thr Glu Cys Glu Ser Cys Ser Gly His Arg
GGA CCT TGC ACG CTC CCC TTC AGT GAG TGG ACC GAA TGC GAG TCG TGC TCC GGG CAT AGA
               225                     230                     235                     240
Thr Arg Glu Ser Ala Val Ala Phe Asp Tyr Thr Asp Arg Met Cys Ser Gly Asp Thr His
ACC AGG GAA TCC GCA GTA GCA TTT GAT TAC ACT GAC AGA ATG TGC AGT GGT GAC ACA CAC
               245                     250                     255                     260
Glu Val Gln Ser Cys Glu Glu Tyr Cys Ser Gln Asn Ala Gly Gly Gly Ala Gly Gly Asp
GAG GTA CAA AGC TGT GAG GAA TAC TGT TCC CAA AAT GCT GGA GGG GGT GCT GGA GGA GAT
```

FIG. 3A

```
                265                     270                     275                     280
Gly Gly Ala Gly Gly Gly Thr Gly Gly Ser Gly Glu Glu Glu Gly Lys Glu Glu Ser Ser
GGG GGC GCA GGA GGA GGG ACT GGA GGC TCT GGA GAG GAG GAA GGA AAG GAG GAA TCG AGT
                285                     290                     295                     300
Gly Phe Pro Thr Ala Ala Val Ala Gly Gly Val Ala Gly Gly Val Leu Ala Ile Ala Ala
GGA TTT CCA ACT GCA GCT GTA GCC GGT GGC GTG GCT GGG GGA GTC CTC GCC ATT GCT GCG
                305                     310                     315                     320
Gly Ala Gly Ala Phe Thr Gly Leu Ser Gly Gly Ser Ala Ala Ala Ala Thr Glu Ala Gly
GGA GCT GGA GCG TTT TAT GGA TTG AGT GGT GGG AGC GCG GCT GCT GCC ACT GAA GCA GGT
                325                     330                     335                     340
Ala Glu Val Met Thr Glu Ala Gly Thr Ser Asn Ala Ala Glu Val Glu Lys Glu Ser Leu
GCT GAA GTG ATG ACA GAA GCT GGT ACA TCC AAT GCT GCT GAG GTA GAA AAG GAG AGC CTC
                345                     350
Ile Ser Ala Gly Glu Gln Ser Glu Met Trp Ala Ser ***
ATC AGT GCA GGT GAA CAA TCA GAG ATG TGG GCA TCC TAA ATG GAA ACG TCG CCG CCG CGG

GTT TCG AAA AGG TGC GGA TCT TGC ATA TCT GTG AAC GAA TTA TTT ACT AAC ATC GAG CTC

CTT GAC CTC CCG TTG GCA AAT CAT TTA CCA AGC ATC TCT GGC GCA TAG CTT CTT GAA CAA

GAC AAC GGA ATG TCC AAC TGG GGA ACA GCT ATA TTG CGA AGT GTG GTG TTC AAA CCA GAA

GAG AGC ACA GCG TCA TGT TGA TGT TAG GGT TGG GCG CCT CCT TTC CCT TAT TTA TCC CAT

TTC CTC CGC CTT CAT CTT TCC GCC TTC TCT CTG TGC GCC GTA TTT TGG TGT TAT TGG TGC

CTG GCG GAC ATG AAA GAG AGA TTG GCG TTA TTT GCA GCG TGC GCA GGC CAT GGG GG
```

FIG. 4

```
              5                    10                   15                   20
Phe Cys His Ile Gln Gln Pro Arg Phe Glu Asn Phe Cys Asp Ser Tyr Ile Met Leu Leu
TTT TGT CAC ATC CAA CAA CCT CGT TTT GAG AAC TTC TGT GAC AGT TAT ATA ATG CTG CTT
             25                   30                   35                   40
Arg Leu Ser Ala Asp Ser Cys Cys Cys Cys Phe Leu Gln Ser Val His Phe Ala Val
CGA CTG TCC GCT GAC TCC TGC TGC TGC TGC TTT CTC CAA AGT GTC CAC TTT GCA GTT
             45                   50                   55                   60
Gln Ser Val Tyr Arg Leu Ser Asp Leu Glu Ser Glu Phe Leu Tyr Leu Gly Ser Phe Val
CAA AGT GTT TAT CGT CTT TCG GAT CTC GAA AGT GAG TTC CTG TAT CTG GGC AGT TTT GTC
             65                   70                   75
Val Val Asp Ser Ala Leu Ser Arg Gln Leu Gly Gln Leu Leu Gln Leu ***
GTT GTA GAT TCC GCA CTG TCT CGC CAA CTT GGC CAG CTC CTG CAG CTT TAG CGA AGT CGC

ATG CAG ACT GTT GCC CAT ATC ACT TGC AAT TAA GTT GAA GTT TTT ATC TGC ATC AGA GAA

GGG CTG GCG AAG GTC TGC AGC AGG CGG GCT GGC AGC AAA GTT GAA GCT TTC TGC TGC AGC

AGC AAA CTC CGC AGT TCT GTC GTA CGC CAT GTG GGG CTG GCT GCT GCT GCT GCT GCT GCT

GCT GCT GCT GCT GCT GCT GCT TCG CGT TCA GCT TCC TTG AAA CTT TCG ACT GCT GCT AGG

GGG AAA GGC GCA GCT GCG GCG CTC TGG AGT TCA TGT TTG GGA AAG AAG AAC GAA AAG GCA

AAA AGA AAG TAA TAA AAG TTT CAA TTT GGA AGA AAA TAA ATG CCA AAA GGC GGC GAA GTG

TCA TTT AAG TGG AAA GCT AGA GGA AAG CAG ACG CAG CAG CAG GAG TTT CGG CGC TGC TGC

TGT TCC GGA GGA GTG TTC TGC GGA AAA AGA AAG AAA TTG AGA ACA TCC TCC CGC TAA AAT

GCA AAA GAA ATG CAA CTG TCT TCT CAA ATT AAA TAA AGC AGT GGT GAG ATT TGC GAC AGG

AGC TTC GCC ACC GCT GAC GAC GAC GCA GCT CTT GAG GTG TAC AGA CAG CTC GCG GTC ACG

CGG TTA GAA AAA GGA AAG CTG CCG CTT CTT CAC TTC AAA AAT ACT TTT CTG CAG ATA TTC

GAG
```

FIG. 5

```
Leu Leu Leu Leu Leu Leu Gln Gly Ala Glu Cys Leu Leu Arg Ser Ser Lys      20
CTG CTG CTG CTG CTG CTG CAG GGC GCG GAG TGC CTC TTG AGG AGC AGC AAA      60

Leu Ala Leu Glu Ala Leu Leu Glu Gly Ala Arg Val Ala Thr Arg Gly Leu Leu Leu    40
CTG GCC CTC GAG GCC CTC CTC GAG GGG GCA CGC GTT GCA ACG CGG GGT TTG CTG CTG   120

Val Glu Ser Ser Lys Asp Thr Val Leu Arg Ser Ile Pro His Thr Gln Glu Lys Leu Ala    60
GTC GAG AGC AGC AAA GAC ACG GTG CTG CGC AGC ATT CCC CAC ACC CAG GAG AAG CTG GCT  180

Gln Ala Tyr Ser Ser Phe Leu Arg Gly Tyr Gln Gly Ala Ala Gly Arg Ser Leu Gly      80
CAG GCC TAC AGT TCT TTC CTG CGG GGC TAC CAG GGG GCA GCA GGG AGG TCT CTG GGC    240

Tyr Gly Ala Pro Ala Ala Tyr Gly Gln Gln Gln Pro Ser Ser Tyr Gly Ala Pro     100
TAC GGC GCC CCT GCT GCT TAC GGC CAG CAG CAG CCC AGC TAC GGG GCG CCC           300

Pro Ala Ser Ser Gln Gln Pro Ser Gly Phe Phe Trp ***                           113
CCC GCC TCC AGC CAG CAG CCC TCC GGC TTC TTC TGG TAG                            339
```

FIG. 6

```
                          5                      10                      15                      20
    Asp Glu Glu Pro Thr Leu Phe Pro Pro Asp Pro Ala Ser Ala Pro Ala Ala Ala Ala Leu
    GAC GAA GAG CCA ACC CTC TTT CCC CCC GAT CCC GCC TCT GCC CCC GCG GCG GCA GCT CTT
                         25                      30                      35                      40
    Pro Gly Gly Arg Ala Ala Ala Ala Ala Leu Ala Gly Arg Ser Gly Ala Ala Ala Ala Ala
    CCG GGG GGC CGG GCT GCT GCT GCT GCC CTG GCG GGC CGT TCT GGA GCA GCA GCA GCA GCA
                         45                      50                      55                      60
    Ala Ala Gly Gly Ala Pro Val Ser Ala Ala Ala Ala Gly Pro Gly Arg Arg Ala Arg
    GCA GCA GGG GGC GCG CCG GTG TCT GCT GCT GCT GCA GCA GGC CCC GGG CGG CGG GCG CGG
                         65                      70                      75                      80
    Gly Phe Ala Gln Pro Arg Arg Pro Ser Arg Leu Ser Leu Ser Leu Gly Leu Leu Ala Cys
    GGC TTC GCC CAG CCC CGC AGG CCC TCG CGG CTG AGT CTG TCT CTG GGG CTT CTG GCG TGT
                         85                      90                      95                     100
    Leu Val Leu Ala Val Ser Ala Ala Ala Ser Gly Arg Ser Ala Leu Arg Leu Leu Leu Gln
    CTT GTC CTG GCG GTG TCG GCA GCC GCG TCA GGG CGT TCC GCG CTG CGG CTG CTG CTG CAG
                        105                     110                     115                     120
    Gln Gln Gln Gln Gln Gln Gln Gln Arg Arg Ala Trp Glu Arg Arg Asp Ala Ala Leu Ala
    CAG CAG CAG CAA CAA CAG CAG CAG CGG CGG GCG TGG GAA AGG CGC GAC GCA GCT CTC GCT
                        125                     130                     135                     140
    Ala Ala Leu Gly Arg Leu Glu Gly Leu Arg Ala Leu Glu Pro Val Val Ser Ser Leu Ala
    GCA GCA CTT GGC CGC CTC GAA GGC CTG CGA GCC CTG GAG CCC GTA GTG AGC AGC CTG GCG
                        145                     150                     155                     160
    Gly Ala Val Asp Ser Pro Glu Ala Gln Arg Leu Leu Gln Leu Tyr Arg Gln Gln Val Glu
    GGG GCC GTG GAC AGC CCG GAG GCG CAG CGG CTG CTG CAG CTG TAC CGG CAG CAA GTG GAG
                        165                     170                     175                     180
    Val Pro Ala Ala Ala Ala Gly Asp Ala Ala Ala Ala Pro Glu Leu Ala Ala Ala Ala
    GTT CCT GCT GCA GCA GCA GGA GAC GCA GCA GCC GCG CCG GAG CTG GCC GCG GCT GCA
                        185                     190                     195                     200
    Ala Glu Arg Ala Ala Glu Glu Ala Leu Ala Leu Leu Arg Leu Leu His Asp Ala Ala Val
    GCA GAA CGC GCA GCA GAA GAG GCC CTG GCG CTG CTG CGG CTG CTG CAC GAC GCA GCC GTG
                        205                     210
    Gln Glu Ala Ser Leu Leu Glu Ala Ser Gln Arg
    CAG GAG GCC AGC CTG CTG GAG GCC AGC CAG AGA
```

FIG. 7

```
            5                      10                     15                     20
Glu Phe Pro Ser Ser Pro Thr Leu Arg Asp Ser Leu Ser Leu Ala Pro Thr Phe Ser Pro
GAA TTC CCT TCT TCT CCA ACT CTT CGC GAC TCT CTC TCT CTC GCC CCA ACT TTT TCC CCC
                       25                     30                     35                     40
Ala Pro Arg Ser Ser Ser Ser Ser Ser Ser Lys Met Ala Asp Leu Phe Ser Gly Leu
GCG CCC CGC AGC AGC AGC AGC AGC AGC AGC AAA ATG GCA GAC CTC TTC AGC GGA CTC
                       45                     50                     55                     60
Val Gly Gly Val Val Gly Ala Val Ala Ala Ala Asp Leu Pro Ala Glu Gly Glu Arg Ala
GTG GGC GGC GTC GTC GGC GCT GTT GCT GCA GCA GAT TTG CCT GCG GAG GGC GAG AGG GCC
                       65                     70                     75                     80
Pro Arg Pro Ala Pro Gly Thr Ala Trp Thr Cys Cys Cys Ser Lys Leu Gln Glu Gly Ala
CCC CGC CCC GCC CCC GGC ACT GCC TGG ACT TGC TGC TGC AGC AAA CTG CAA GAA GGG GCC
                       85                     90                     95                     100
Arg Glu Leu Glu Gly Phe Val Gln Gln Leu Ser Phe Val Ala Gly Lys Leu Ala Cys Cys
CGC GAG CTG GAG GGT TTT GTG CAG CAG CTG AGT TTT GTT GCA GGG AAG CTG GCC TGC TGC
                       105                    110                    115                    120
Leu Arg Val Gly Ala Glu Gln Leu Ala Arg Cys Ala Ala Glu Gly Arg Leu Pro Ser Ser
CTG CGG GTG GGG GCG GAG CAG CTG GCG CGC TGC GCT GCG GAG GGG CGG CTG CCC AGC AGC
                       125                    130                    135                    140
Ser Ser Ser Ser Ser Cys Cys Ala Leu Leu Gln Leu Glu Lys Gln Asp Leu Glu Gln Ser
AGC AGC AGC AGC AGC TGC TGC GCG CTG CTG CAG CTC GAG AAG CAG GAC CTC GAG CAG AGC
                       145                    150                    155                    160
Leu Glu Ala Gly Lys Gln Gly Ala Glu Cys Leu Leu Arg Ser Ser Lys Leu Ala Leu Glu
CTC GAG GCC GGC AAG CAG GGC GCG GAG TGC CTC TTG AGG AGC AGC AAA CTG GCC CTC GAG
                       165                    170                    175                    180
Ala Leu Leu Glu Gly Ala Arg Val Ala Ala Thr Arg Gly Leu Leu Leu Val Glu Ser Ser
GCC CTC CTC GAG GGG GCC CGC GTT GCA GCA ACG CGG GGT TTG CTG CTG GTC GAG AGC AGC
                       185                    190                    195                    200
Lys Asp Thr Val Leu Arg Ser Ile Pro His Thr Gln Glu Lys Leu Ala Gln Ala Tyr Ser
AAA GAC ACG GTG CTG CGC AGC ATT CCC CAC ACC CAG GAG AAG CTG GCT CAG GCC TAC AGT
                       205                    210                    215                    220
Ser Phe Leu Arg Gly Tyr Gln Gly Ala Ala Ala Gly Arg Ser Leu Gly Tyr Gly Ala Pro
TCT TTC CTG CGG GGC TAC CAG GGG GCA GCA GCG GGG AGG TCT CTG GGC TAC GGG GCC CCT
                       225                    230                    235                    240
Ala Ala Ala Tyr Gly Gln Gln Gln Gln Pro Ser Ser Tyr Gly Ala Pro Pro Ala Ser Ser
GCT GCT GCT TAC GGC CAG CAG CAG CAG CCC AGC AGC TAC GGG GCG CCC CCC GCC TCC AGC
                       245
Gln Gln Pro Ser Gly Phe Phe Trp ***
CAG CAG CCC TCC GGC TTC TTC TGG TAG
```

FIG. 8

```
                  5                      10                       15                      20
Glu Phe Pro Ser Ser Pro Thr Leu Arg Asp Ser Leu Ser Leu Ala Pro Thr Phe Ser Pro
GAA TTC CCT TCT TCT CCA ACT CTT CGC GAC TCT CTC TCT CTC GCC CCA ACT TTT TCC CCC
                 25                      30                       35                      40
Ala Pro Arg Ser Ser Ser Ser Ser Ser Ser Lys Met Ala Asp Leu Phe Ser Gly Leu
GCG CCC CGC AGC AGC AGC AGC AGC AGC AGC AAA ATG GCA GAC CTC TTC AGC GGA CTC
                 45                      50                       55                      60
Val Gly Gly Val Val Gly Ala Val Ala Ala Ala Asp Leu Pro Ala Glu Gly Glu Arg Ala
GTG GGC GGC GTC GTC GGC GCT GTT GCT GCA GCA GAT TTG CCT GCG GAG GGC GAG AGG GCC
                 65                      70                       75                      80
Pro Arg Pro Ala Pro Gly Thr Ala Trp Thr Cys Cys Cys Ser Lys Leu Gln Glu Gly Ala
CCC CGC CCC GCC CCC GGC ACT GCC TGG ACT TGC TGC TGC AGC AAA CTG CAA GAA GGG GCC
                 85                      90                       95                     100
Arg Glu Leu Glu Gly Phe Val Gln Gln Leu Ser Phe Val Ala Gly Lys Leu Ala Cys Cys
CGC GAG CTG GAG GGT TTT GTG CAG CAG CTG AGT TTT GTT GCA GGG AAG CTG GCC TGC TGC
                105                     110                      115                     120
Leu Arg Val Gly Ala Glu Gln Leu Ala Arg Cys Ala Ala Glu Gly Arg Leu Pro Ser Ser
CTG CGG GTG GGG GCG GAG CAG CTG GCG CGC TGC GCT GCG GAG GGG CGG CTG CCC AGC AGC
                125                     130                      135                     140
Ser Ser Ser Ser Ser Cys Cys Ala Leu Leu Gln Leu Glu Lys Gln Asp Leu Glu Gln Ser
AGC AGC AGC AGC AGC TGC TGC GCG CTG CTG CAG CTC GAG AAG CAG GAC CTC GAG CAG AGC
                145                     150                      155                     160
Leu Glu Ala Gly Lys Gln Gly Ala Glu Cys Leu Leu Arg Ser Ser Lys Leu Ala Leu Glu
CTC GAG GCC GGC AAG CAG GGC GCG GAG TGC CTC TTG AGG AGC AGC AAA CTG GCC CTC GAG
            3262
                165                     170                      175                     180
Ala Leu Leu Glu Gly Ala Arg Val Ala Ala Thr Arg Gly Leu Leu Leu Val Glu Ser Ser
GCC CTC CTC GAG GGG GCC CGC GTT GCA GCA ACG CGG GGT TTG CTG CTG GTC GAG AGC AGC
                185                     190                      195                     200
Lys Asp Thr Val Leu Arg Ser Ile Pro His Thr Gln Glu Lys Leu Ala Gln Ala Tyr Ser
AAA GAC ACG GTG CTG CGC AGC ATT CCC CAC ACC CAG GAG AAG CTG GCT CAG GCC TAC AGT
                205                     210                      215                     220
Ser Phe Leu Arg Gly Tyr Gln Gly Ala Ala Ala Gly Arg Ser Leu Gly Tyr Gly Ala Pro
TCT TTC CTG CGG GGC TAC CAG GGG GCA GCA GCG GGG AGG TCT CTG GGC TAC GGG GCC CCT
                225                     230                      235                     240
Ala Ala Ala Tyr Gly Gln Gln Gln Gln Pro Ser Ser Tyr Gly Ala Pro Pro Ala Ser Ser
GCT GCT GCT TAC GGC CAG CAG CAG CAG CCC AGC AGC TAC GGG GCG CCC CCC GCC TCC AGC
                245
Gln Gln Pro Ser Gly Phe Phe Trp ***
CAG CAG CCC TCC GGC TTC TTC TGG TAG
                                        ─)
```

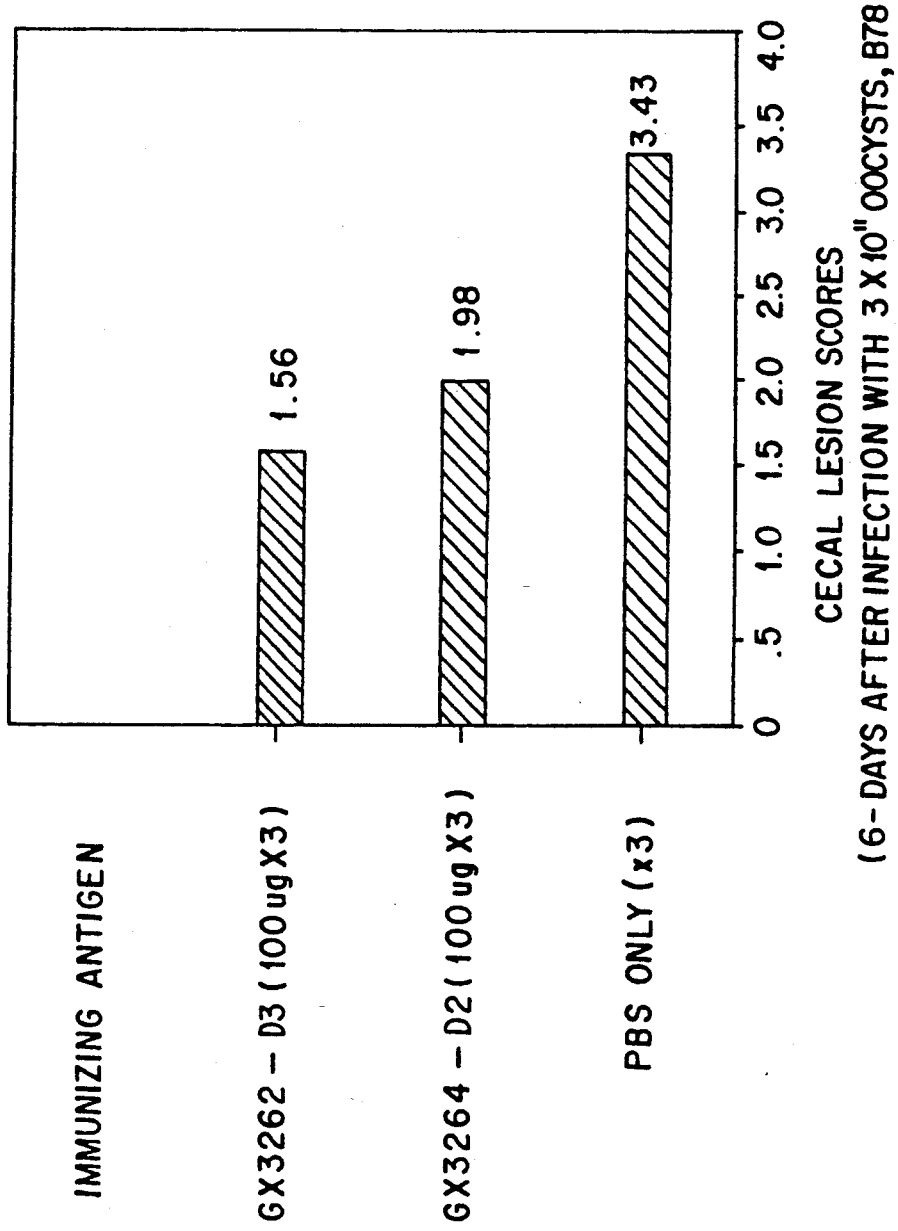

25 KD COCCIDIAL ANTIGEN OF *EIMERIA TENELLA*

CROSS-REFERENCE TO RELATED APPLICATIONS

This application is a continuation of U.S. patent application Ser. No. 07/215,162, filed Jul. 5, 1988, (now abandoned), which is a continuation-in-part application of U.S. patent application Ser. No. 746,520, filed Jun. 19, 1985, a continuation-in-part of U.S. patent application Ser. No. 627,811, filed Jul. 5, 1984, both now abandoned.

FIELD OF THE INVENTION

This invention is in the field of avian coccidiosis and is directed to recombinant antigenic peptides of avian coccidia and to the genes that encode the peptides. These antigenic peptides may be used in a vaccine against avian coccidia.

BACKGROUND OF THE INVENTION

Coccidiosis is a disease of both invertebrates and vertebrates, including man, caused by intracellular parasitic protozoa which generally invade the epithelial cells lining the alimentary tract and the cells of associated glands. The crowded conditions under which many domestic animals are raised have contributed to increased incidence of the disease. Virtually every domestic animal is susceptible to infection, and distribution of the parasite is world-wide. Coccidiosis is therefore the cause of significant economic loss throughout the world.

The poultry industry suffers particularly severe losses, with coccidiosis being the most economically important parasitic disease of chickens. Since 1949, preventive anticoccidials have been used but have not been totally effective. Losses due to morbidity from coccidiosis, including reduced weight gains and egg production, and decreased feed conversion, persist. The cost of coccidiosis in broiler production has been estimated at ½ to 1 cent per pound. Based on an annual production of 3,000,000,000 broilers annually in the United States, losses would total between 60 and 120 million dollars. To this figure must be added the cost of anticoccidials estimated at 35 million dollars. These impressive figures emphasize the importance of reducing the incidence of coccidiosis in chickens.

Of the nine genera of coccidia known to infect birds, the genus Eimeria contains the most economically important species. Various species of Eimeria infect a wide range of hosts, including mammals, but nine species have been recognized as being pathogenic to varying degrees in chickens: *Eimeria acervulina, E. mivati, E. mitis, E. praecox, E. hagani, E. necatrix, E. maxima, E. brunetti* and *E. tenella.*

Although the Eimeria are highly host specific, their life cycles are similar. The developmental stages of the avian coccidia can be illustrated by the species *Eimeria tenella*, which proliferates in the cecum of the chicken.

The life cycle of the Eimeria species begins when the host ingests previously sporulated oocysts during ground feeding or by inhalation of dust. Mechanical and chemical action in the gizzard and intestinal tract of the chicken ruptures the sporulated oocyst, liberating eight sporozoites. The sporozoites are carried in the digestive contents and infect various portions of the intestinal tract by penetration of epithelial cells. Subsequent life stages involve asexual multiple fission, the infection of other epithelial cells, development of gametes, and fertilization to produce a zygote which becomes an oocyst which is passed out of the host with the droppings. The oocyst undergoes nuclear and cellular division resulting in the formation of sporozoites, with sporulation being dependent upon environmental conditions. Ingestion of the sporulated oocyst by a new host transmits the disease.

Of all species of Eimeria, *E. tenella* has received the most attention. *E. tenella* is an extremely pathogenic species, with death often occurring on the fifth or sixth day of infection.

Before the use of chemotherapeutic agents, poultry producers' attempts to control coccidiosis were limited to various management programs. These programs were directed toward attempts at sanitation through disinfection, or by mechanical removal of litter. Despite these efforts, sufficient oocysts usually remained to transmit the disease.

One means of combating the hazards of coccidia is immunization. This method involves feeding to the poultry a small dose of oocysts of each of the species of coccidia during the first weeks of life. However, dosage control has proven difficult as birds ingest daughter oocysts, with some birds developing severe coccidiosis and others remaining susceptible. Also, since this procedure produces mixed infections, sometimes adequate immunity does not develop to all species given. In addition, immunity development is too slow for use with broiler production.

Another means of combating coccidia is drug treatment after the poultry is infected. One drug that has been used is sulfanilamide which has shown anticoccidial activity against six species of coccidia. However, unless the drug treatment of the flock is quickly initiated after diagnosis of the disease, medication may be started too late to be effective.

Ideally, the best method for combating coccidia is preventive medication. Since the advent of the use of sulfonamide drugs, over forty compounds have been marketed for preventive medication against coccidia. There have been many problems with the use of such drugs, including anticoccidial contamination of layer flock feeds, inclusion of excessive anticoccidial drugs in the feed causing toxicity in the birds and omission of the anticoccidial from the feed resulting in coccidiosis outbreaks. A particularly frustrating problem has been the development of drug-resistant strains of coccidia. Moreover, there is a potential for drug residues being deposited in the meat.

Clearly, available methods for the control of coccidiosis have met with limited success, and the need for a safe, efficient, and inexpensive method of combating avian coccidiosis remains.

The development of an effective anticoccidial vaccine is a desirable solution to the problem of disease prevention. Vaccines produced by traditional methods will require extensive development. There are reports of the production of attenuated strains through passage in embryos or cell culture. While this approach may eventually lead to successful vaccines, not all the important species of Eimeria have been adapted to growth in culture or embryos such that they are capable of completing their life cycle.

Genetic engineering methodology presents the opportunity for an alternative approach to vaccine development. It is known that genes encoding antigenic proteins of pathogenic organisms can be cloned into microorganisms. The antigenic proteins then can be expressed at high levels, purified, and used as vaccines against the pathogenic organism. These antigenic proteins have the advantage of being noninfectious and are potentially inexpensive to produce. Such "subunit vaccines" have been prepared from antigen genes for a number of viruses such as hepatitis, herpes simplex and foot and mouth disease virus. An alternate approach is to produce "synthetic vaccines", small chemically-synthesized peptides, whose sequence is chosen based upon the amino acid sequence translation of viral antigen DNA. The advantages of such "synthetic vaccines" over traditional vaccination with attenuated or killed pathogenic organisms have been summarized by Lerner in *Nature* 299:592-596 (1982).

It is now possible to produce foreign proteins, including eukaryotic proteins, in prokaryotic organisms such as gram positive or gram negative bacteria. The process involves the insertion of DNA (derived either from enzymatic digestion of cellular DNA or by reverse transcription of mRNA) into an expression vector. Such expression vectors are derived from either plasmids or bacteriophage and contain: (1) an origin of replication functional in a microbial host cell; (2) genes encoding selectable markers, and (3) regulatory sequences including a promoter, operator, and a ribosome binding site which are functional in a microbial host cell and which direct the transcription and translation of foreign DNA inserted downstream from the regulatory sequences. To increase protein production and stability, eukaryotic proteins are often produced in prokaryotic cells as a fusion with sequences from the amino-terminus of a prokaryotic protein. β-Galactosidase or the product of one of the *E. coli* tryptophan operon genes have been used successfully in this manner. Expression vectors have also been developed for expression of foreign proteins in eukaryotic host cells, e.g., yeast and chinese hamster ovary tissue culture cells.

Host cells transformed with expression vectors carrying foreign genes are grown in culture under conditions known to stimulate production of the foreign protein in the particular vector. Such host cell/expression vector systems are often engineered so that expression of the foreign protein may be regulated by chemical or temperature induction. Proteins which are secreted may be isolated from the growth media, while intracellular proteins may be isolated by harvesting and lysing the cells and separating the intracellular components. In this manner, it is possible to produce comparatively large amounts of proteins that are otherwise difficult to purify from native sources.

Such microbially produced proteins may be characterized by many well-known methods, including the use of monoclonal antibodies, hereinafter referred to as "MCAs," which are homogeneous antibodies that react specifically with a single antigenic determinant and display a constant affinity for that determinant, or by use of polyvalent antibodies derived from infected birds, which react with a variety of different antigens and often with multiple determinants on a single antigen.

Alternate technology to the production of "subunit" or "synthetic" vaccines is the use of a fowl pox virus vector. The pox virus vaccinia has a long history of use as a vaccine and has been employed to virtually irradicate smallpox in humans. It now has been demonstrated that vaccinia virus can be effectively genetically engineered to express foreign antigens (Smith et al., Nature 302:490-495 (1983); Panicali et al., Proc. Natl. Acad. Sci. U.S.A. 80:5364-5368 (1983); Mackett et al., J. of Virology 49:857-864 (1984)) and the engineered viruses can serve as a live vaccine against other viruses and infections besides smallpox. Fowl pox virus is very similar to vaccinia virus and many of the methods developed for vaccinia for the creation of recombinants expressing foreign antigens can be applied to fowl pox. Attenuated fowl pox virus engineered to produce avian coccidia antigens thus is another method to produce an anticoccidial vaccine. Live vaccines have the advantage of being inexpensive to produce and are characterized by the production of rapid immunity development.

A second type of live vaccine results in the presentation of antigen in the gut where coccidia normally invades. This method utilizes secretion or outer surface expression of the antigen by harmless bacteria introduced into the intestinal microbial population by incorporation in feed. Secretion is obtained by fusion of an antigen gene to the gene coding for a protein which is normally secreted, leaving the necessary secretion signal sequence intact. Outer surface expression is achieved b fusion of the antigen genes to the genes that code for proteins normally localized on the outer surface. (T. Silhavy, U.S. Pat. No. 4,336,336.) This type of live vaccine is especially advantageous since manufacturing costs are minimal and the immune response stimulated is of a type particularly effective against coccidia invasion of the gut.

SUMMARY OF THE INVENTION

This invention relates to novel recombinant antigenic peptides of avian coccidiosis, and fragments thereof containing antigenic determinants, and to the genes that encode the antigenic peptides. It has now been found that particular polypeptides present in avian cells infected with coccidiosis, when purified and isolated, contain an antigenic determinant or determinants which can elicit an antibody response. This invention also relates to vaccines made using the novel antigenic peptides of avian coccidiosis and to methods of immunizing chickens against avian coccidia.

BRIEF DESCRIPTION OF THE FIGURES

FIG. 1 gives the DNA sequence and amino acid sequence of the 5'→3' strand of CDNA encoding the GX5401 antigen gene.

FIG. 2 gives the DNA sequence and amino acid sequence of the 5'→3' strand of CDNA encoding the GX3264 antigen gene.

FIGS. 3 and 3A gives the DNA sequence and amino acid sequence of the 5'→3' strand of CDNA encoding the GX3271 antigen gene.

FIG. 4 gives the DNA sequence and amino acid sequence of the 5'→3' strand of CDNA encoding the GX3273 antigen gene.

FIG. 5 gives the DNA sequence and amino acid sequence of the 5'→3' strand of CDNA encoding the GX3262 antigen gene.

FIG. 6 gives the DNA sequence and amino acid sequence of the 5'→3' strand of CDNA encoding the GX3276 antigen gene.

FIG. 7 gives the DNA sequence and amino acid sequence of the 5'→3' of CDNA encoding the GX3262(Ext4c) antigen gene.

FIG. 8 gives a comparison of GX3262 and GX3262(ext4c) coding sequences.

FIG. 9 is a bar graph showing the results of GX3262 and GX3264 antigens to provide protective immunity in one-day-old chickens against an *E. tenella* infection.

Figure 10:
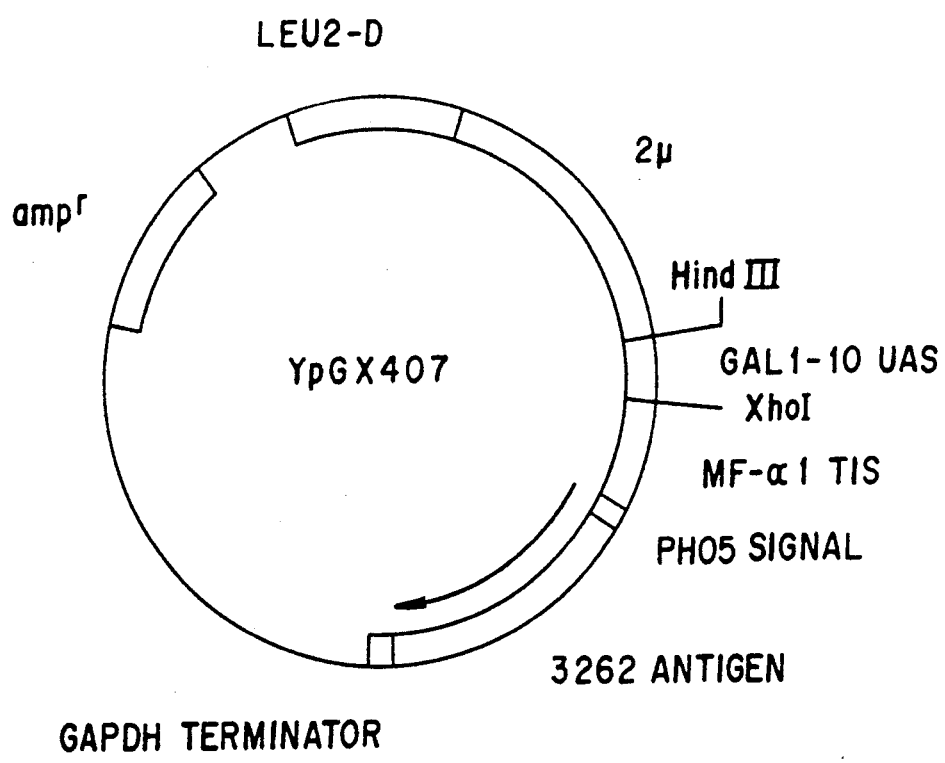
FIG. 10 shows the plasmid YpGX407.

As is well known in the art, due to the degeneracy of the genetic code, the DNA sequences given in the Figures for the genes and antigenic peptides of this invention may be encoded by different DNA than those represented. Thus, knowledge of an amino acid sequence does not necessarily lead to a precise genetic sequence coding therefor. In all of the Figures with DNA and amino acid sequences the sequence is given as the 5' to 3' strand. The abbreviations have the following standard meanings:

A is deoxyadenyl
T is thymidyl
G is deoxyguanyl
C is deoxycytosyl
GLY is glycine
ALA is alanine
VAL is valine
LEU is leucine
ILE is isoleucine
SER is serine
THR is threonine
PHE is phenylalanine
TYR is tyrosine
TRP is tyryptophan
CYS is cysteine
MET is methionine
ASP is aspartic acid
GLU is glutamic acid
LYS is lysine
ARG is arginine
HIS is histidine
PRO is proline
GLN is glutamine
ASN is asparagine.

DETAILED DESCRIPTION OF THE PREFERRED EMBODIMENT

The present invention relates to recombinant antigenic peptides, and fragments thereof containing antigenic determinants, that can elicit an antibody response against avian coccidiosis, and to the cloned genes that encode the antigenic peptides. These antigenic peptides, and the fragments thereof containing antigenic determinants, will bind with a specific monoclonal antibody or with polyvalent antibodies from infected chickens, directed against an antigenic protein of avian coccidia.

The antigenic peptides of this invention may be used for several applications: (1) by labelling the peptide(s), they can be used as a type-specific probe(s); (2) the peptide(s) can be used in an avian coccidia assay to detect antibodies against the coccidia; (3) antibodies may be prepared from the antigenic peptide(s); (4) the peptide(s) can be used for preparing vaccines against avian coccidiosis.

Scientists at the Animal Parasitology Laboratory, U.S. Department of Agriculture (USDA) have produced a series of monoclonal antibodies (MCA) against nine species of avian coccidia of the genus Eimeria (i.e., *E. tenella, E. acervulina, E. maxima, E. necatrix, E. brunetti, E. mivati, E. mitus, E. meleagrimitis* and *E. adenoides*). (Danforth, *J. Parisitol.* 68:392–397 (1982))

The MCA cell lines were produced by injecting mice with sporozoites that had been isolated from oocysts of each of the species named above. Spleen cells from these mice were fused with mouse myeloma cells and cell lines derived from single cells were isolated, characterized, and analyzed for species specificity.

The United States Department of Agriculture also has produced polyvalent immune chicken serum by immunizing chickens (which were raised in coccidia-free environments) against *E. tenella* by infecting the chickens with doses of from $10^2$–$10^5$ oocysts and recovering serum from the birds at 4–14 days post-infection.

This antiserum was tested in an enzyme-linked immunosorbent assay (ELISA), using extracts of *E. tenella* sporozoites as an antigen, and the antiserum was shown to contain antibodies against *E. tenella* sporozoite proteins. The various MCAs were tested by an indirect immunofluorescent antibody test for binding to air-dried sporozoites. Binding patterns seen for the MCAs varied from a general internal fluorescence (similar to that seen with the chicken antiserum) to fluorescence on the tip, pellicle, and refractile body of the parasite, or a combination thereof. (Danforth and Augustine, *Poultry Science* 62:2145–2151 (1983)). Some MCAs bound to sporozoites of species other than the one to which they were raised, while others were species specific. A few MCAs were tested, in vitro, and found to inhibit the parasite's penetration of epithelial cells and development, to varying degrees. (Danforth, *Amer. J. Vet. Res.* 44:1722–1727 (1983)).

Antibodies directed against coccidial-antigens are used to identify, by immunological methods, transformed cells containing DNA encoding coccidial antigens. The MCAs are used as a tool for identifying cells containing DNA sequences encoding coccidial antigens that are either species specific or common to all nine species. Screening transformants with polyvalent chicken antiserum is used to identify DNA sequences encoding a wide spectrum of coccidial proteins which are antigenic in chickens upon infection. DNA sequences from the transformants thus identified then may be incorporated into a microorganism for large scale protein production. The antigenic proteins, as native proteins or as hybrids with other proteins, may be used as vaccines to immunize birds to protect them from subsequent infection.

As used herein, the term "antigenic" or "antigenic determinant" is meant immunologically cross-reactive antigenic determinants with which a given antibody will react. Therefore, the antigenic peptides of this invention will include chemically synthesized peptides, peptides made by recombinant DNA techniques, and antibodies or fragments thereof which are anti-idiotypic towards the determinant of the peptides of this invention.

Several procedures may be used to construct a microorganism that produces an antigenic protein that binds with a monoclonal or polyvalent antibody that is directed against an antigenic protein of avian coccidia. One such procedure can be divided into the following major stages, each of which is described more fully herein: (1) recovery and isolation of messenger RNA (mRNA) found in organisms of the genus Eimeria; (2) in vitro synthesis of complementary DNA (cDNA), using coccicidia mRNA as a template; (3) insertion of the CDNA into a suitable expression vector and transformation of bacterial cells with that vector; and, (4) recovery and isolation of the cloned gene or gene fragment. This route is referred to as the mRNA route. The advantage to this route is that only "expressed" genes are cloned, reducing the number of individual transformants required to represent the entire population of genes.

An alternative procedure can be divided into the following major stages which will also be described more fully herein: (1) recovery and isolation of nuclear DNA found in organisms of the genus Eimeria; (2) fragmentation of the DNA and insertion into a suitable vector; (3) transformation into a suitable microbial host; (4) selection of transformants containing a gene which specifies the antigen of interest; and, (5) recovery and isolation of the cloned gene or gene fragment. This route is referred to as the nuclear DNA route. The advantage to this route is that all genes are cloned, allowing the identification of genes not expressed at the time from which mRNA is isolated. These may include genes which are expressed during stages of the life cycle which are not easy to isolate.

After recovery and isolation of the cloned gene that is derived from the procedures discussed above, the cloned DNA sequence is advantageously transferred to a suitable expression vector/host cell system for large scale production of the antigenic protein.

The DNA sequence that is to be isolated encodes an antigenic protein that will elicit an immune response when administered to chickens which will protect them from subsequent infections. It is not necessary to isolate a complete coccidial gene encoding such a protein, since those portions of the protein termed antigenic determinants are sufficient for triggering a protective immune response (Lerner, supra). This antigenic determinant should be on the surface of the folded microbially-produced protein to trigger the response (Lerner, supra).

In the mRNA route, the sequence may be isolated from the sporozoite life stage of the parasite. It has been demonstrated that part of the protective immune response in chickens is directed against the sporozoite. Scientists at the U.S. Department of Agriculture detected antibodies to sporozoite proteins in immune chicken serum, which also indicates that the sporozoite is a life stage that can be affected by an immune response in chickens. Antigenic proteins isolated from other life stages also may be effective as vaccines.

MCAs or polyvalent antibodies which bind to various sporozoite proteins can be used to identify cloned DNA sequences encoding those proteins. Such proteins can be isolated and used to elicit a protec-tive immune response in chickens.

Sporozoites can be obtained from oocysts by excystation using the method of Doran and Vetterling, Proc. Helminthol Soc. Wash. 34:59-65 (1967), and purified by the leucopak filter technique of Bontemps and Yvore, Ann. Rech. Vet. 5:109-113 (1974). Although the method of Doran and Vetterling has been found suitable for obtaining sporozoites from oocysts, any method is suitable as long as the nucleic acids within the sporozoites remain intact. Also, sporozoite mRNA may be isolated from intact sporulated oocysts, which contain the sporozoites.

mRNA Route

Isolation of mRNA coding for the antigenic proteins of interest is advantageously accomplished by lysis of intact sporulated oocysts under conditions which minimize nuclease activity. This is accomplished using a modification of the procedure described by Pasternak et al., Molec. Biochem. Parisitol. 3:133-142 (1982). Total RNA may be isolated by grinding the oocysts with glass beads in a solution containing sodium dodecyl sulfate (SDS) and proteinase K. After denaturation and degradation of oocyst proteins, the RNA is isolated by extraction of the solution with phenol and precipitation with ethanol. Oligo (dt)-cellulose chromatography then can be used to isolate mRNA from the total RNA population.

Proteins coded for by the isolated mRNA can be synthesized, in vitro, using a cell-free translation system. A number of cell-free translation systems have been devised, such as wheat germ extract (Martial et al., Proc. Nat'l Acad. Sci. U.S.A. 74:1816-1820 (1977)), rabbit reticulocyte lysate (Pelham and Jackson, Eur. J. Biochem. 67:247-256 (1976)), and oocytes from Xenopus laevis (Sloma et al., Methods in Enzymology 79:68 (1981)). The rabbit reticulocyte lysate is preferred for the testing of sporozoite mRNA. The rabbit reticulocyte lysate can be supplemented with a radioactively labeled amino acid, such as [$^{35}$S]-methionine, so that the resulting proteins contain a tracer. The various protein products may be reacted with polyvalent chicken antisera or MCAs previously described, followed by reaction with goat anti-chicken IgG in the case of the polyvalent antibodies and Staphylococcus aureus Protein A, or in the case of the MCAs, just Protein A. Protein A binds any of the mouse or goat antibodies to form an immunoprecipitated complex. The products of the translation and of the immunoprecipitation are visualized by gel electrophoresis followed by fluorography. The mRNA fractions found to produce proteins that react with the antisera in this system are used for ds-cDNA synthesis. Alternatively, to avoid missing any antigens which are not synthesized efficiently, in vitro, or are not immunoprecipitated efficiently, total mRNA is used for CDNA synthesis.

Synthesis of CDNA employs avian myeloblastosis virus reverse transcriptase. This enzyme catalyzes the synthesis of a single strand of DNA from deoxynucleoside tri-phosphates on the mRNA template. (Kacian and Myers, Proc. Nat'l Acad. Sci. U.S.A. 73:2191-2195 (1976).) The poly r(A) tail of mRNA permits oligo(dT) (of about 12-18 nucleotides) to be used as a primer for CDNA synthesis. The use of a radioactively labeled deoxynucleoside triphosphate facilitates monitoring of the synthesis reaction. Generally, a $^{32}$p-containing deoxynucleoside triphosphate, such as [$\alpha$-$^{32}$P]dCTP, may be used advantageously for this purpose. The CDNA synthesis is generally conducted by incubating a solution of the mRNA, the deoxynucleoside triphosphates, the oligo(dT)12-18 and reverse transcriptase for 10 minutes at 46° C. The solution also preferably contains small amounts of actinomycin D and dithiothreitol to promote full length synthesis. (Kacian and Myers, supra.) After incubation, ethylenediaminetetraacetic acid (EDTA) is added to the solution, and the solution is extracted with phenol:chloroform. The aqueous phase is advantageously purified by gel filtration chromatography, and the cDNA-mRNA complex in the eluate is precipitated with alcohol.

The mRNA can be selectively hydrolyzed in the presence of the cDNA with dilute sodium hydroxide at an elevated temperature. Neutralization of the alkaline solution and alcohol precipitation yields a single-stranded CDNA copy.

The single-stranded CDNA copy has been shown to have a 5' poly (dT) tail, and to have a 3' terminal hairpin structure, which provides a short segment of duplex DNA. (Efstratiadis et al., Cell 7:279-288 (1976)). This 3' hairpin structure can act as a primer for the synthesis of a second DNA strand. Synthesis of this second strand is conducted under essentially the same conditions as the synthesis of the CDNA copy, except that the Klenow fragment of E. coli DNA polymerase I (Klenow et al., Eur. J. Biochem. 22:371-381 (1971)) is substituted for reverse transcriptase. The duplex CDNA recovered by this procedure has a 3' loop, resulting from the 3' hairpin structure of the single-stranded CDNA copy. This 3' loop can be cleaved by digestion with the enzyme, S1 nuclease, using essentially the procedure of Ullrich et al., Science 196:1313-1319 (1977). The S1 nuclease digest may be extracted with phenol-chloroform, and the resulting ds-cDNA precipitated from the aqueous phase with alcohol.

For purposes of amplification and selection, the ds-cDNA prepared as described above is generally inserted into a suitable cloning vector, which is used for transforming appropriate host cells. Suitable cloning vectors include various plasmids and phages, but a bacteriophage lambda is preferred.

For a cloning vector to be useful for the expression of foreign proteins which are to be detected with antibodies, it should have several useful properties. Most importantly, it should have a cloning site within a gene which is expressed in the host being used. There should also be a means of controlling expression of the gene. The vector should be able to accept DNA of the size required for synthesis of the desired protein product and replicate normally. It is also useful to have a selectable property which allows identification of vectors carrying inserts. A cloning vector having such properties is the bacteriophage λgt11 (ATCC 37194) (Young and Davis, Proc. Nat'l Acad. Sci. U.S.A. 80:1194-1198 (1983)). This vector has a unique EcoRI site near the end of the bacterial gene coding for β-galactosidase. That site can be used for insertion of foreign DNA to make hybrid proteins made up of β-galactosidase and the foreign gene product. The expression of β-galactosidase is under control of the lac promoter and can be induced by the addition of isopropyl-β-D-thiogalactopyranoside (IPTG). The Xgt11 phage contains 43.7 kb of DNA which is considerably smaller than wild type λ. This allows insertion of pieces of DNA up to 8.3 kb in length, before the DNA becomes too large to fit inside the phage head. Because DNA is inserted into the gene for β-galactosidase, transformants having inserts can easily be distinguished from those which do not by looking for 0-galactosidase activity. An indicator dye, 5-bromo-4-chloro-3-indolyl-β-D-galactoside (Xgal), can be incorporated with agar plates. β-galactosidase cleaves this molecule to give a blue product, thus allowing examination of the cultures for the presence of active β-galactosidase. Those plaques having inserts are colorless on X-gal plates because the insertion of foreign DNA into the β-galactosidase gene has eliminated its activity.

The ds-cDNA can be conveniently inserted into the phage by addition of EcoRI linkers to the DNA and ligation into the EcoRI-cut λgt11 DNA. After ligation of the CDNA into the phage DNA, the DNA is packaged, in vitro, into λ phage heads (Enquist and Sternberg, Methods in Enzymology 68:281-298 (1979) and those phages are used to infect a suitable λ-sensitive host. With the proper choice of host, the phage may be screened as plaques or lysogens (colonies).

Aside from the E. coli/bacteriophage λgt11 system described, many other host/vector combinations have been used successfully for the cloning of foreign genes in E. coli (Principles of Gene Manipulation, 2nd Ed., Old and Primrose, Univ. of California Press, 32-35, 46-47 (1981)) including "open reading frame" vectors, described in detail later.

The foregoing discussion has focused on cloning procedures in gram negative bacteria, e.g., E. coli. Alternatively, foreign genes may be cloned into plasmid vectors that will transform and replicate in a gram positive bacterium such as Bacillus subthis (Old and Primrose, supra, pp. 51-53) or in a eukaryotic microorganism such as yeast (Old and Primrose, supra, pp. 62-68). Cloning vectors have been constructed which transform both yeast and E. coli . Such vectors are termed "shuttle vectors" and may be transferred, along with the cDNA they carry, between the two host microorganisms (Storms, et al., Journal of Bacteriology 140:73-82 (1979); and Blanc et al., Molec. Gen. Genet. 176:335-342 (1979). Shuttle vectors also exist which replicate in (and may carry cloned genes into) both E. coli and B. subthis (Old and Primrose, supra, at p. 53). Vectors derived from the other bacteriophages such as M13 have also proven useful in the cloning of foreign genes (Old and Primrose, supra, Chap. 5). Any of these techniques can be employed, if desired, in the constructions of the present invention.

The DNA described herein may be inserted into the above vectors by various techniques including homopolymeric tailing, blunt-end ligation or by use of linker molecules (Old and Primrose, supra, at p. 92).

Many immunological methods for screening clone banks for those expressing a desired protein are known and include procedures described by Engvall and Pearlman, Immunochem t@r 8:871-874 (1971); Koenen et al., The European Molecular Biology Organization Journal, Vol. 1, No. 4, pp. 509-512 (1982); Broome et al., Proc. Natl. Acad. Sci., U.S.A. 75:2746-2749 (1978); Villa-Komaroff et al., Proc. Natl. Acad. Sci., U.S.A. 75:3727-3731 (1978); Anderson et al., Methods in Enzymology 68:428-436 (1979); Clarke et al., Methods in Enzymology 68:436-442 (1979); Ehrlich et al., Methods in Enzymology 68:443-453 (1979); Kemp et al., Proc. Natl. Acad. Sci., U.S.A. 78:4520-4524 (1981).

By the cloning procedures outlined, thousands of recombinant bacteriophage are generated. In order to screen them for production of coccidial antigens, two antibody screens can be utilized. Both screening methods depend upon expression of the coccidial antigenic protein either alone or as a fusion protein with a bacterial gene. In the examples included herein, the coccidial antigens are produced as fusions with E. coli β-galactosidase. The screening methods, therefore, depend on expression of the fusion product and detection of the product by reaction with antibodies, either monoclonal or polyvalent, directed against that antigen.

The recombinant bacteriophages can be used to infect a suitable E. coli host which allows the formation of phage plaques on agar (or agarose) plates. The plaques can be transferred to nitrocellulose membranes while being induced with IPTG. The proper antibodies are then reacted with the filters. After reaction of the primary antibodies with the filters, the positive reactions are detected by reaction with either [$^{125}$I] *Staphylococcus aureus* Protein A or a second antibody conjugated with horseradish peroxidase.

Alternatively, the recombinant bacteriophages can be used to infect an *E. coli* host in which lysogens are produced at a high frequency. In this case, the transformants can be screened as colonies. The colonies are grown on a cellulose acetate filter under non-induced conditions. After the colonies have reached a suitable size, the cellulose acetate filter is placed over a nitrocellulose filter which is on an agar plate containing IPTG. The colonies are incubated at elevated temperatures to induce phage production, while expression of the $\beta$-galactosidase gene is induced by inclusion of IPTG. After a suitable incubation period, during which some lysis of the colonies occurs with release of proteins through the cellulose acetate filter onto the nitrocellulose filter, the cellulose acetate filter is removed. The nitrocellulose filter is processed as described above for screening of plaques.

The phages giving positive signals in the antibody-screening procedure can be shown to contain sequences coding for coccidial proteins by excision of the DNA originally inserted into the phage DNA and examination of the ability of that DNA to hybridize with coccidia mRNA or coccidia genomic DNA. The nucleotide sequence of the cDNA insert is determined using the methods of Sanger et al., *Proc. Natl. Acad. Sci., U.S.A.* 74:5463–5467 (1977); or Maxam and Gilbert, *Proc. Natl. Acad. Sci., U.S.A.* 74:560–S64 (1977).

Nuclear DNA Route

Another method of cloning coccidial antigens begins with isolation of nuclear DNA from oocysts. This DNA is then broken into fragments of a size suitable for insertion into a cloning vector. To obtain such fragments, one can use mechanical shearing methods such as sonication or high-speed stirring in a blender to produce random breaks in the DNA. Intense sonication with ultrasound can reduce the fragment length to about 300 nucleotide pairs. (Old and Primrose, supra, p. 20.) Alternatively, nuclear DNA may be partially digested with DNAseI, which gives random fragments, with restriction endonucleases, which cut at specific sites, or with mung bean nuclease in the presence of formamide, which has been shown with some related organisms (McCutchan, T. F., et al. *Science* 225:625–628 (1984)) to produce DNA fragments containing intact genes.

These nuclear DNA fragments may be inserted into any of the cloning vectors listed for the cloning of cDNA in the mRNA experimental method. If the nuclear DNA is digested with a restriction endonuclease, it can be inserted conveniently into a cloning vector digested with the same enzyme, provided the vector has only one recognition site for that enzyme. Otherwise, DNA fragments may be inserted into appropriate cloning vectors by homopolymeric tailing or by using linker molecules (Old and Primrose, supra, at p. 92).

Advantageously, the nuclear DNA fragments are cloned into "open reading frame" vectors which are designed to simultaneously clone and express foreign genes or fragments thereof. Several such vectors are known in the art, including those described by Weinstock et al., *Proc. Natl. Acad. Sci., U.S.A.* 80:4432–4436 (1983); Keonen et al., *The European Molecular Biology Organization Journal* 1, 4, pp. 509–512 (1982); Ruther et al., 79:6852–6855 (1982); Young and Davis, supra; and Gray et al. *Proc. Natl. Acad. Sci. U.S.A.* 79:6598–6602 (1982).

Open reading frame (ORF) vectors have been used to clone both prokaryotic and eukaryotic genomic DNA or cDNA. These vectors generally contain a bacterial promoter operably linked to an amino terminal fragment of a prokaryotic gene. A carboxy terminal fragment of a gene which encodes a product for which an assay is known (e.g., the *E. coli* lacZ gene which encodes $\beta$-galactosidase) is located downstream. The sequences between the amino terminal gene fragment and the lacz fragment include restriction endonuclease recognition sites useful for insertion of foreign genes and, in some cases, also place the lacZ fragment out of reading frame for translation with respect to the amino terminal gene fragment. When foreign DNA is inserted into these vectors (by blunt end ligation, homopolymeric tailing, ligation of cohesive termini, or the use of linkers), a certain percentage of recombinants will have received foreign DNA of a length that puts the lacZ gene in phase with the reading frame set by the amino terminal gene fragment. The result is production of a "tribrid" protein comprising the polypeptides encoded by the amino terminal gene fragment, the cloned DNA, and the lacZ gene. Such recombinants are identified on MacConkey agar plates or on agar plates containing "Xgal" (5-bromo-4-chloro-3-indolyl-$\beta$-D galactoside) because the $\beta$-galactosidase activity of the tribrid protein cleaves the dye in such plates, turning colonies red (MacConkey agar) or blue (Xgal). $\beta$-galactosidase can carry a wide range of protein sequences at its amino terminus and still retain biological activity. Alternatively, the insert may be inserted to inactivate a gene by interrupting the sequence. The insert may be in the correct reading frame to produce a hybrid gene consisting of the amino-terminus of the bacterial gene and sequences from the insert gene at the carboxy terminus.

Only recombinants receiving exons (i.e., coding sequences of genes, which have no stop codons) which are in-frame with respect to the amino terminal gene fragment are detected by this method. ORF vectors are useful for cloning genes for which no DNA or protein sequence data exists, if antibodies against the gene product exist. Screening of the clone bank may be accomplished by immunological methods which make RNA or DNA hybridization probes unnecessary. The immunological screening methods mentioned for the mRNA route can be used.

Plasmid DNA is isolated from transformants found to be "positive" by the above screening methods. The nuclear DNA inserts of these plasmids are then subjected to DNA sequencing. Once the nucleotide sequence is known, it is possible by known methods to chemically synthesize all or part of the cloned coccidial genes. The synthesis of fragments of the cloned genes, followed by insertion of the gene fragments into expression vectors as described below and reaction of the polypeptides produced with MCAs allows detection of those portions of the gene which are antigenic determinants.

Once a cloned DNA sequence is identified as encoding a protein that binds antibodies directed against coccidial proteins, it may be transferred to expression vectors engineered for high-level production of the desired antigenic protein. The expression vectors are transformed into suitable microbial host cells for production of the antigenic protein.

Coccidial antigens advantageously may be produced at high levels in *E. coli* as a fusion protein comprising the antigen and an amino terminal portion of the β-subunit of the enzyme tryptophan synthetase (the product of the *E. coli* trpB gene). This fusion is accomplished by inserting a DNA sequence encoding a coccidial antigen into a plasmid vector carrying the trpB gene.

The expression vector used may be one in which expression of the fusion antigenic protein is highly regulatable, e.g., by chemical induction or temperature changes. An expression vector with such regulatory capability is the plasmid pGX2606, which contains a hybrid $\lambda O_L P_R$ regulatory region as described in co-pending application Ser. No. 534,982 filed Sep. 23, 1983. Host expression vector systems in which expression of foreign proteins is regulatable have the advantage of avoiding possible adverse effects of foreign protein accumulation as high cell densities are reached. Some investigators have proposed that expression of gene fragments such as those encoding antigenic determinants may avoid the deleterious effects that expression of the entire antigenic protein would have on *E. coli* host cells. (Helfman et al., *Proc. Natl. Acad. Sci., U.S.A.* 80:31-35 (1983)).

Coccidial antigens also may be produced in high levels as fusions at the carboxy-terminal of *E. coli* β-galactosidase, as they are directly obtained by use of the cloning vector λgt11. The fused β-galactosidase-coccidia antigen gene is transferred with all of the associated regulatory elements to a small plasmid, where synthesis of the gene product is regulated by the lac promoter, which is transferred along with the fusion gene from the phage to the plasmid. Such a small plasmid is PGX1066 (plasmid pGX1066 is present in *E. coli* strain GX1186, ATCC 39955) which carries the gene for ampicillin resistance and has a bank of restriction sites which are useful for insertion of DNA fragments. Synthesis of the fusion protein is induced by addition of IPTG, the inducer of the lac operon.

An effective subunit vaccine against avian coccidiosis may consist of a mixture of antigen proteins derived from several species of Eimeria. Alternatively, production costs may be decreased by producing two or more antigen proteins as one fusion protein thus reducing the required number of fermentations and purifications. Such a fusion protein would contain the amino acid sequence comprising an antigenic epitope of each antigen protein (or repetitions of those sequences) with variable amounts of surrounding nonantigenic sequence. A hybrid gene designed to code for such a protein in *E. coli* would contain bacterial regulatory sequence (promoter/operator) and the 5' end of an *E. coli* gene (the ribosome binding site and codons for several amino acids) to ensure efficient translation initiation followed by the coding sequences for the antigenic epitopes all fused in the same reading frame.

*E. coli* cells transformed with the expression vector carrying a cloned coccidial antigen sequence are grown under conditions that promote expression of the antigenic polypeptide. The antigenic protein is then purified from the cells and tested for ability to elicit an immune response in chickens that will protect them from subsequent Eimeria infections. The purified protein may be used to immunize the birds. The purified protein may be combined with suitable carriers and adjuvants and administered to birds in their feed or by injection. Alternatively, live microorganisms containing the DNA sequences encoding the coccidial antigens may be fed to chickens. Such microorganism are advantageously those which normally inhabit the avian intestinal tract, such as *E. coli* or coryneform bacteria.

In a particularly preferred system, the microorganisms are transformed with an expression vector in which the sequences encoding the coccidial antigen are fused in frame to a gene or gene fragment encoding a host cell outer membrane protein or secreted protein, such as the *E. coli* lamb protein, the λ receptor. The antigenic protein is therefore continuously presented in the host at the location of infection by the parasites. It is known that foreign proteins fused in expression vectors to outer membrane or secreted proteins have been presented at the cell surface or secreted from their host cells. (Weinstock, supra, and Silhavy, U.S. Pat. No. 4,336,336 which is herein incorporated by reference.)

In another preferred system for development of live vaccines, an attenuated fowl pox virus expression vector is utilized. Fowl pox has the capacity to accommodate several coccidia genes allowing the production of multivalent vaccines. Currently, attenuated fowl pox virus is utilized as a vaccine to protect commercial flocks against fowl pox infection. Virus preparation and treatment of birds with fowl pox virus genetically engineered to produce coccidia antigens is the same as the conventional methods of pox vaccine use currently practiced.

Pox viruses are among the most complex viruses known with very high molecular weight double-stranded DNA genomes. With the most studied pox virus, vaccinia, it has been demonstrated that the pox genome can easily accommodate inserts of foreign DNA capable of coding for foreign antigenic proteins (Smith et al., supra; Panicali et al., supra; Mackett et al., supra). When a foreign gene is incorporated into the pox virus genome under the control of a pox promoter regulatory sequence, the foreign antigen is expressed upon infection in the cytoplasm of the cell where the pox virus replicates. Successful insertion and expression of coccidia antigen genes within the fowl pox genome is dependent upon identifying a nonessential region of the pox DNA for antigen gene insertion and ensuring an active pox promoter is situated 5' of the desired coccidia gene.

Insertion of DNA into the pox genome is accomplished by in vivo recombination. Pox DNA is not infectious presumably because its cytoplasmic location requires the presence of pox virus specific RNA and DNA polymerases that are normally carried into the cell by the virion. DNA sequence information from vaccinia virus (Weir and Moss, *J. of Virology* 46:530-537 (1983); Venkatesan et al., *Cell* 125:805-813 (1981)) demonstrates sequence patterns in regulatory regions that are likely to be unique to vaccinia genes and thus not recognized by cellular enzymes. Because the pox DNA is not infectious, foreign DNA insertion into the fowl pox genome is accomplished by in vivo recombination as has been demonstrated with vaccinia to occur at high frequency (Weir et al., *Proc. Natl. Acad. Sci., U.S.A.* 79:1210-1214 (1982)). A fowl pox virus infection of chick embryo fibroblasts is followed by transfection using the $CaCl_2$ precipitation technique (Graham et al., *Virology* 52:456-457 (1973); Stow et al., *J. Virology* 28:6182-192 (1978)) with plasmid DNA that includes the coccidia antigen gene placed under the control of a promoter functional in fowl pox, and DNA sequence homology with fowl pox. During the course of the infection recombination occurs. If a coccidia DNA sequence is inserted within the fowl pox homologous sequence on the transfected plasmid, upon recombination the coccidia DNA sequence is, in some cases, inserted into the pox virus genome. The infected cells and virus from a recombination attempt are harvested and fresh chick embryo fibroblast cells grown as a monolayer in tissue culture are infected at a low multiplicity such that individual plaques resulting from an initial single virus infection can be identified using conventional techniques. Desired recombinant viruses are identified using an in situ hybridization technique (Villarreal and Berg, *Science* 196:183-185 (1977)) using radioactive coccidia DNA sequence as probe. Alternatively, viral DNA immobilized on nitrocellulose paper prepared from cells infected by plaque purified virus or cells infected with pools of potential recombinant viruses can be used for identification of desired recombinant viruses. Immunological screening of fixed cells (Gremer et al., *Science* 228:737-740 (1985)) is an alternative to hybridization.

The region of fowl pox DNA included in the plasmid vector must be from a nonessential region, and is chosen by randomly testing segments of fowl pox DNA for regions that allow recombinant formation without seriously affecting virus viability using the method described above. Fowl pox DNA is purified (Muller et al., *J. Gen. Virology* 38:135 (1977); Gafford et al., *Virology* 89:229 (1978)), randomly sheared to about 3 kilobases and cloned into a small bacterial plasmid, such as pGx1066, creating several different isolates. Foreign DNA must be inserted into the fowl pox portion of the plasmids before testing the effect of recombination upon virus viability. To accomplish this, *E. coli* transposon insertions such as 6 (Guyer, *Methods in Enzymology* 101:362-369 (1983)) can be readily placed within the fowl pox portion of the plasmid. Cotransfections that result in viable fowl pox recombinants containing $\lambda\delta$ sequence identify desirable nonessential fowl pox DNA for use in cotransfection plasmids.

Fowl pox DNA regions with partial sequence homology to the thymidine kinase gene of vaccinia identified by hybridization experiments are also useful for inclusion in the cotransfection plasmid since the thymidine kinase gene of vaccinia has been shown to be nonessential (Weir (1982), supra; Mackett et al., *Proc. Natl. Acad. Sci., U.S.A.* 79:4927-4931 (1982); Hruby and Ball, *J. Virology* 43:403-408 (1982)).

Placement of the coccidia antigen gene under the control of a fowl pox promoter is carried out by conventional in vitro manipulation of the plasmid before concurrent transfection and fowl pox infection. Promoter sequences useful for driving expression of the coccidia antigens could be identified by determination of the DNA sequence located 5' to fowl pox genes. Promotor sequences are then synthesized chemically and included in the plasmid vector adjacent to endonuclease cloning sites within the fowl pox homologous region of the plasmid. Putative promoter sequences identified through DNA sequencing of vaccinia DNA (Venkatesan et al. (1981), supra; Weir and Moss (1983), supra) are also chemically synthesized and compared with fowl pox promoters for optimal effect. Putative fowl pox promoters are verified by cloning them 5' of a test gene with an easily measured translation product such as chloramphenicol acetyltransferase (Gorman et al., *Molecular and Cellular Biology* 2:1044-1057 (1982)) in a bacterial plasmid. The plasmid is used to transfect fowl pox infected tissue culture cells and the cells are assayed for transient expression of the test gene.

Vaccinia virus has a broad host range and does infect chickens. Thus the vectors and methods already developed for vaccinia could be utilized to develop vaccines for avian coccidia and coccidiosis in any other genus included in the vaccinia host range. This approach requires caution since vaccinia is severely pathogenic to a small proportion of the human population.

A good alternative to pox vectors would be to utilize a herpes virus such as Marek's Disease virus or Herpes virus of turkeys. Attenuated forms of both viruses are currently used as live vaccines to prevent Marek's disease in poultry. Similar to pox viruses, herpes viruses have large double stranded DNA genomes and are good candidates for genetic engineering using in vivo recombination methods similar to those developed for vaccinia. The advantage of engineering Marek's disease virus to also provide protection against coccidia infection is that coccidia protection is provided at no additional production cost above the Marek's Disease Vaccine that is already generally in use.

The production of coccidia antigen by fowl pox recombinants is verified by immunological analysis of the protein produced in chick embryo fibroblast tissue culture cells after infection and also by testing the circulating antibody of birds infected with recombinant fowl pox virus for cross reaction with whole coccidia or protein isolated from coccidia of the appropriate species.

The cloned antigenic proteins used in vaccines above are tested for their ability to elicit an immune response in chickens that protects the birds from subsequent infection by any of the important species of Eimeria, including *E. tenella, E. acervulina, E. brunetti, E. mivati, E. maxima* and *E. necatrix*. The cloning procedures described above may be repeated until DNA sequences encoding coccidial antigens that collectively protect chickens against coccidiosis are isolated and used as a vaccine by the methods above.

In addition to cloned antigenic proteins which may be useful as vaccines to protect against coccidiosis, another useful alternative which may be derived from cloning antigen genes is the use of small, synthetic peptides in vaccines (see Lerner, supra). After the sequence of antigenic proteins is determined, it is possible to make synthetic peptides based on that sequence. The peptides are conjugated to a carrier protein such as hemocyanin or serum albumin and the conjugate then can be used to immunize against coccidia.

It is contemplated that the procedures described may also be used to isolate antigenic proteins from other coccidia species that can be used in vaccines to protect other domestic animals from coccidiosis.

The following examples are supplied in order to illustrate, but not necessarily limit, the present invention.

EXAMPLE I

Preparation of RNA from *Eimeria tenella* oocysts

Total RNA was isolated from *E. tenella* oocysts using a modification of procedures described by Pasternak et al., *Molec. Biochem. Parasitol.* 3:133-142 (1981). Oocysts of *E. tenella* were purified free of bacterial and fungal contamination by treatment with 5.25% sodium hypochlorite solution at 0°-4° C. for 15 minutes followed by extensive washing with cold water. Oocysts were then separated from other debris by centrifugation over a cushion of 0.6M sucrose in a Sorvall HB-4 rotor for 5 minutes at 5,000 rpm at 4° C. Oocysts float on top of the cushion while most of the other debris is pelleted at the bottom of the centrifuge tube. The purified oocysts were again washed thoroughly with cold water and were stored at 4° C. in Hank's medium (Gibco, Grand Island, New York) containing 10 units/ml penicillin and 10 μg/ml streptomycin.

For isolation of total RNA, the oocysts were pelleted by centrifugation and resuspended in 5 ml (per 1 g wet weight) of lysis buffer consisting of 10 mM Tris-acetate, 75 mM sodium acetate, 2 mM EDTA, 1% SDS, and 200 μg/ml Proteinase K (pH 7.5). One half volume of acid-washed glass beads (0.45–0.50 mm) were added to the suspension. The tube was mixed on a vortex mixer for 2 minutes at room temperature. Breakage of the oocysts and sporozoites was monitored microscopically. The resulting mixture of lysed oocysts was centrifuged at 15,000 rpm for 15 minutes at 4° C. in a Sorvall SM-24 rotor. The supernatant solution was removed, the pellet was resuspended in 5 ml of the lysis buffer, the mixture was centrifuged as before, and the supernatant solution was combined with the first one. The solution was incubated at 37° C. for 30 minutes. The solution was extracted twice with an equal volume of phenol (saturated with lysis buffer minus SDS and Proteinase K), once with chloroform, and the RNA in the aqueous layer was precipitated by addition of 0.1 volume of 2.4M sodium acetate, pH 5.5., and 2.5 volumes of ethanol. After 1 hour at $-20°$ C., the RNA was collected by centrifugation in a Sorvall HB-4 rotor at 13,000 rpm at 4° C. The RNA was dried in a vacuum desiccator, dissolved in sterile water, and stored at $-80°$ C. The absorbance at 260 nm was measured to determine the amount RNA present. An $A_{260}$ of 1.0 corresponds to an RNA concentration of about 40 μg/ml. From 1 gram (wet weight) of oocysts, approximately 0.5 mg of total RNA was obtained.

EXAMPLE II

Preparation of Polyadenylated mRNA from Total RNA

Poly(A)+ mRNA was obtained by hybridization to oligo (dT)-cellulose. The column of oligo (dt)-cellulose was equilibrated with binding buffer having a composition of 10 mM Tris-HCl pH 7.4, 1 mM EDTA, and 500 mM NaCl, and the total RNA preparation of Example I was cycled through the column two times. Unbound RNA was removed by washing the column with several column volumes of binding buffer. Elution buffer having a composition of 10 mM Tris-HCl, pH 7.4, 1 mM EDTA, was used to wash bound poly(A)* RNA from the column, which was precipitated as before. The following describes the process of oligo (dt)-cellulose column chromatography in greater detail.

Stock Solutions and Materials:

Oligo (dT) binding buffer (1X): 10 mM Tris-HCl, pH 7.4, 1 mM EDTA, 0.5 M NaCl.

Oligo (dT) binding buffer (2X): 10 m4 Tris-HCl, pH 7.4, 1 mM EDTA, 1.0 M NaCl.

Oligo (dT) elution buffer: 10 mM Tris-HCl, pH 7.4, 1 mM EDTA.

Procedure:

1. Pellets of precipitated RNA were thoroughly drained of ethanol, dried, resuspended in oligo (dT) elution buffer, and absorbances at 260 nm and 280 nm were determined; $A_{260/280}$ should be about 2, and an $A_{260}$ of 1.0 corresponds to an RNA concentration of about 40 μg/ml.

2. The RNA solution was then adjusted to 5–10 mg/ml with the elution buffer and heated for 5 minutes at 65° C., quick-cooled and mixed with an equal volume of the 2X oligo (dT) binding buffer.

3. The RNA solution was chromatographed on an oligo (dT)-cellulose column (about 2 grams oligo (dt)-cellulose in a 1.5×15 cm column) which had previously been washed with 5 column volumes of 1X oligo (dT) binding buffer; the column was eluted at a rate of about 10–15 ml/hr.

4. The column effluent was recycled once, then retained as "poly A+" RNA and stored under ethanol.

5. The oligo (dt)-cellulose column was washed with about 5 column volumes of IX oligo (dT) binding buffer, and the RNA was eluted with about two to three column volumes of elution buffer and collected in fractions of about 25–35 drops with the aid of a Gilson fraction collector.

6 Absorbances of the fractions were determined and the UV-absorbing material pooled to produce the 1X oligo (dT) purified "poly A+ RNA".

7. At this point, the pooled RNA fractions were either rechromatographed on an oligo (dt)-cellulose column to further purify the poly A+ RNA (step 7a) or precipitated with ethanol and stored until used or further purified on oligo (dt)-cellulose (step 7b):

a. Rechromatography: after step 6, the volume of the pooled fractions was determined, the solution was heated to 65° C. for 5 minutes, quick-cooled and diluted with an equal volume of 2X oligo (dT) binding buffer and passed over the same oligo (dT) column which had been thoroughly washed with several column volumes of elution buffer and several volumes of binding buffer; RNA was processed as in steps 3, 4, 5, and 6 and precipitated by addition of sodium acetate to 0.3M and 2.5 volumes of 95% ethanol ($-20°$ C. to $-80°$ C.). The resulting precipitate was designated "2X purified oligo (dT) poly A+RNA."

b. Ethanol precipitation followed by rechromatography: if after step 6 it was necessary to interrupt the procedure, the RNA solution was made 0.3M in sodium acetate and 2.5 volumes of 95% ethanol were added; after at least 2 hours at $-20$ C, RNA was pelleted by centrifugation at 10,000xg for 15 min., washed 2X with 70% ETOH and drained; RNA was then processed, starting with step 1, but the initial concentration of poly A+RNA was about 1 mg/ml or less.

8. After use, the oligo (dt)-cellulose column was cleaned by passing 2–3 column volumes of 0.1N NAOH through it. The column was then washed with 5–7 column volumes of oligo (dT) binding buffer containing 0.02% sodium azide, and stored at room temperature.

EXAMPLE III

Characterization of mRNA Preparations by in vitro Translation

Coccidia mRNA isolated in Example II was translated in a rabbit reticulocyte lysate which had been made dependent on added RNA by treatment with micrococcal nuclease (commercially available from New England Nuclear, Boston, Massachusetts, and other sources). The reagents were prepared according to the manufacturer's instructions, and 0.1–0.5 μg of RNA were added. [$^{35}$S]-methionine was included to radioactively label the translation products. Samples run as controls were water (no RNA), rabbit globin mRNA, and poly A+ RNA from the coccidia RNA preparation. The samples were incubated at 30° C. for 90 minutes. Incorporation of label was followed by measuring incorporation of [$^{35}$S]-methionine into trichloroacetic acid (TCA)-precipitable material. To 0.5 ml of 0.5 NAOH, 0.5% H$_2$O$_2$, 20 mg/ml casamino acids was added 2 µl of the translation mix. After incubation at 37° C. for 30 minutes, 0.5 ml of 0.5 HCl were added, followed by 2.5 ml of 10% TCA. After 15 minutes in an ice bath, the precipitated material was collected by filtration on a 2.5 cm nitrocellulose filter disc, the filter was washed 3 times with 5 ml of 5% cold trichloroacetic acid (TCA), and the filters were dried under a heat lamp. The dry filters were placed in scintillation vials with 5 ml of OCS TM (Amersham, Arlington Heights, Illinois) and counted in a liquid scintillation counter. Generally, about 5- to 20-fold stimulation of incorporation relative to the water control was observed.

The products of the in vitro translation were separated on a 12.5% SDS-polyacrylamide gel run according to Laemmli, *Nature* 227:680-685 (1970). The products were visualized by fluorography (Laskey and Mills, *Eur. J. Biochem.* 56:335-341 (1975)).

EXAMPLE IV

Synthesis of Double-Stranded cDNA

Stock Solutions and Materials for First Strand cDNA Synthesis 0.5M Tris HCl, pH 8.3
1.4M KCl
0.25M MgCl$_2$ 0.05M dATP, pH 7.0
0.5M dGTP, pH 7.0
0.05M DCTP, pH 7.0
0.05M dTTP, pH 7.00
[α-$^{32}$P]dCTP, 400 Ci/mmol, 1 mCi/ml (Amersham), stabilized aqueous solution
0.01M dithiothreitol (DTT)
Oligo (dT)$_{12-18}$ 250 µg/ml (Collaborative Research)
Actinomycin D, 500 µg/ml (Calbiochem)
0.2M disodium ethylenediaminetetraacetate (EDTA), pH 8.0
Avian myeloblastosis virus (AMV) reverse transcriptase, approximately 10,000 units/ml (obtained from Life Sciences Inc., St. Petersburg, Florida).

All buffers and salt solutions were autoclaved. The other solutions were prepared with sterile glass-distilled water and were stored in sterile containers. All stock solutions were stored frozen. All enzymes described in this and the other examples were obtained commercially and used according to the manufacturer's specifications unless otherwise noted.

Procedure:

As a template for cDNA synthesis, mRNA prepared in Example II was employed. In order to follow the synthesis, a radioactive marker ([α-$^{32}$P]dCTP) was used. This allows monitoring of all steps by counting Cerenkov radiation, which does not result in any loss of sample. For each µg of mRNA, 2 µCi of [α-$^{32}$P]dCTP at a specific activity of 400 Ci/mmol were used. The radioactive material was added to a 2X reaction mixture consisting of 0.1 M Tris HCl, pH 8.3, 140 mM KCl, 20 mM MgCl$_2$, 1 mM DATP, 1 mM DCTP, 1 mM DGTP, 1 mM TTP, and 0.4 mM DTT. This solution was kept on ice. To this solution was added mRNA (50 µg/ml, final concentration), oligo (dT)$_{12-18}$ (25 µg/ml), actinomycin D (40 µg/ml), AMV reverse transcriptase (800 units/ml), and enough water to dilute the 2X mix to 1X. After 5 min. on ice, the reaction mixture was incubated at 46° for 10 min. Following the incubation, EDTA was added to a final concentration of 25 mM. The solution was extracted one time with an equal volume of phenol:chloroform (1/1; v/v) and the aqueous phase was chromatographed on a column of Sephadex G-100 (0.7 × 20 cm) equilibrated with 10 mM Tris.HCl, pH 8.0, 1 mM EDTA, 0.1 M NaCl. The mRNA:cDNA hybrid in the excluded volume was precipitated by addition of 0.1 volume of 3 M sodium acetate and 2 volumes of 95% ethanol ($-20°$ C. to $-80°$ C.). In order to remove the mRNA moiety, the pelleted hybrid was dissolved in 300 µl 0.1M NAOH and incubated at 70° C. for 20 minutes. The solution was cooled on ice and neutralized with 30 µl of 1N HCl. The cDNA was precipitated as described above.

Stock Solutions and Materials for Second Strand cDNA Synthesis 0.5M potassium phosphate, pH 7.4
0.25M MgCl$_2$
0.1M Dithiothreitol (DTT)
0.05M dATP, pH 7.0
0.05M dGTP, pH 7.0
0.05M dCTP, pH 7.0
0.05M dTTP, pH 7.0
*E. coli* DNA polymerase I (Klenow fragment), approximately 5,000 units/ml (Boehringer-Mannheim)
10X S1 nuclease buffer: 0.5M sodium acetate, pH 4.5; 10 mM ZnSO$_4$, 2M NaCl, 5% glycerol.

Procedure:

It was not necessary to use a radioactive label in the second strand, since the first strand was labeled. A 2X reaction mixture consisting of 0.2M potassium phosphate, pH 7.4, 20 mM MgCl, 2 mM DTT, 0.4 mM each of dATP, dGTP, dCTP, and dTTP was prepared and kept on ice. To this mixture was added an aqueous solution of cDNA containing the Klenow fragment of *E. coli* DNA polymerase I (100 units/ml. final concentration), and water was added to dilute the reaction mixture to 1X. The solution was incubated overnight at 15° C. After the incubation, EdTA was added to 25 mM, the solution was extracted once with an equal volume of phenol:chloroform (1/1; v/v), and the aqueous phase was chromatographed on a 0.7 × 20 cm column of Sephadex G−100 equilibrated with 10 mM Tris- HCl, pH 8.0, 1 mM EdTA, and 0.1M NaCl. The DNA in the excluded fractions was precipitated with ethanol as described above.

At this point, the ds cDNA is in the form of a hairpin. The single-stranded loop was removed by digestion with S1 nuclease. The ds cDNA was dissolved in water and 0.1 volume of 10X S1 buffer was added. An appropriate amount of S1 nuclease was added and the solution was incubated 20 min. at 37° C. The amount of enzyme added was determined empirically for each enzyme preparation, since the activity varied from one preparation to another. This was done by measuring the decrease in TCA-precipitable counts from the ds cDNA. Generally, a decrease of 20-40% was observed. The S1-digested cDNA was extracted once with phenol:chloroform and the cDNA in the aqueous phase was precipitated with ethanol as described above.

EXAMPLE V

Addition of Linkers to cDNA

For insertion of the cDNA into the EcoRI site of the λgt11 vector, EcoRI linkers were added to the ends of the cDNA molecules. To prevent cleavage of the cDNA molecules with EcoRI, the cDNA was first methylated with EcoRI methylase.

Stock Solutions and Materials:

5×EcoRI methylase buffer—0.5M Tris-HCl, pH 8.0, 0.05M EdTA.

8 mM S-adenosyl methionine (SAM)—solution in 0.01M $H_2SO_4$, pH 2, 10% ethanol.

1 mg/ml bovine serum albumin (BSA) solution in water, sterile filtered.

8 base pair EcoRI linkers—10$A_{260}$/ml, obtained from Collaborative Research, Waltham, Massachusetts.

10 mM ATP, pH 7.0.

10×T4 polynucleotide kinase buffer—0.7M Tris-HCl, pH 7.6, 0.1M $MgCl_2$; 50 mM dithiothreitol. [$\gamma$-$^{32}$P]-ATP—10 mCi/ml., >2,000 Ci/mmol, stabilized aqueous solution.

10×T4 ligase buffer—0.5M Tris-HCl, pH 7.8., 0.1M $MgCl_2$, 0.2M dithiothreitol.

10×DNA polymerase buffer—0.5M Tris-HCl, pH 7.2, 0.1M $MgSO_4$, 2 mM dATP, dCTP, dGTP, dTTO mixture, pH 7.0. 1 mM dithiothreitol.

10X EcoRI buffer—1.0M Tris-HCl, pH 7.5, 0.5M NaCl, 0.05M $MgCl_2$.

Procedure:

The cDNA from Example IV was dissolved in 20 μl of 5×EcoRI methylase buffer, SAM was added to 80 JIM, BSA was added to 0.4 mg/ml, water was added to bring the volume to 99 μl, and 1 μl of EcoRI methylase (20,000 units/ml, New England Biolabs) was added. The reaction was incubated at 37° C. for 60 minutes. The reaction was then extracted 2 times with phenol and ethanol precipitated. The methylated cDNA was collected by centrifugation and dried.

Before addition of the linkers, the cDNA was treated with DNA polymerase I (Klenow fragment) in the presence of deoxynucleoside triphosphates to make the ends of the cDNA blunt. The cDNA was dissolved in 24 μl of 1X DNA polymerase buffer containing 80 μM each dATP, dCTP, dGTP, and dTTP. Two units of DNA polymerase (Klenow fragment) were added and the reaction mixture was incubated at 23° C. for 10 minutes. EdTA was added to 20 mM and the cDNA was extracted 2 times with phenol, once with $CHCl_3$, and ethanol precipitated. The cDNA, which was EcORI-methylated and blunt-ended, was collected by centrifugation, washed once with cold 70% ethanol, and dried.

To prepare the linkers for addition to the cDNA, they must first be phosphorylated. 400 picomoles of 8-base pair EcoRI linkers were phosphorylated in 1X polynucleotide kinase buffer with 20 μCi of [$\gamma$-$^{32}$P]-ATP and 5 units of polynucleotide kinase. The reaction was incubated at 37° C. for 15 minutes. Unlabeled ATP was then added to 1 mM and the reaction was incubated at 37° C. for 30 minutes. The enzyme was inactivated by heating the reaction at 65° C. for 10 minutes. 160 picomoles of the phosphorylated linkers were then ligated to the cDNA. The blunt-ended, methylated cDNA was dissolved in 10 μl of water, 160 picomoles of linkers were added, 10×T4 ligase buffer was added to 1X, ATP was added to 1 mM, and 2 units of T4-DNA ligase (Boehringer Mannheim) were added. The reaction mixture (a total of 20 μl) was incubated at 15° C. for 16 hours. The ligase was inactivated by heating the reaction at 65° C. for 10 minutes.

At this point, the cDNA had multiple linkers at the ends. Excess linkers were removed by digestion with EcoRl.

The ligation reaction was diluted with 5 μl of 10×EcoRI buffer, 5 μl of 1 mg/ml BSA and 19 μl of water. Prior to addition of EcoRI, 1 μl of the mix was removed for analysis by gel electrophoresis. Ten units of EcoRI (New England Biolabs, 10 units/μl) were added and the reaction was incubated at 37° C. for 1 hour. The reaction was extracted 1 time with phenol and run over a column of Sepharose CL—4B in 10 mM Tris-HCl, pH 8, 1 mM EdTA, 0.3M NaCl. This removed excess linkers and short pieces of DNA (up to about 100 b.p.). The fractions containing the cDNA were pooled and ethanol precipitated. The cDNA was collected by centrifugation.

EXAMPLE VI

Preparation of Recombinant Bacteriophage DNA

Bacteriophage λgt11 DNA (available from the American Type Culture Collection, Accession Number 37194) prepared by standard methods (Maniatis et al., *Molecular Cloning,* Cold Spring Harbor, (1982)) was linearized by digestion with ECORI, phenol-extracted, and precipitated with ethanol. Fifty ng cDNA from Example V was mixed with 1 μg EcoRl-cut λgt11 (a molar ratio of approximately 2:1) in 50 mM Tris-HCl, pH 7, 10 mM $MgCl_2$, 20 mM dithiothreitol, 1 mM ATP, and 1 unit of T4-DNA ligase (Boehringer Mannheim) added. The ligation mixture was incubated for 16 hours at 15° C. A small portion of the reaction mix was analyzed by agarose gel electrophoresis. The desired product at this point was high molecular weight, concatameric DNA, which is in the form required for efficient packaging into empty bacteriophage λ heads.

EXAMPLE VII

Packaging of the Recombinant DNA into Bacteriophage λ Heads and Transfection into *E. coli*

The recombinant DNA prepared in Example VI was packaged into bacteriophage heads for introduction into *E. coli,* by procedures described by Enquist and Sternberg, *Methods in Enzymology* 68:281-298 (1979). Packaging extracts are available commercially (Promega Biotec, Madison, Wisconsin, and other sources) and were used according to the manufacturer's instructions. The ligated DNA was mixed with the packaging extracts (50 μl), incubated at 23° C. for 2 hours, the phages were diluted to 0.5 ml with 10 mM $MgSO_4$, 10 MM Tris-HCl, pH 7.5., 0.01% gelatin, and a few drops of chloroform were added to the mixture. The packaged phages were stored at 4° C.

As a host for titration and propagation of the phage, *E. coli* strain Y1088 (AlacU169 supE supF hdsR$^-$ hsdM$^+$ metB trpR tonA21 ProC::Tn5 (pMC9)) (available from the American Type Culture Collection, accession number 37195) was used. The host strain was grown overnight at 37° C. in LB-broth containing 0.2% maltose, to induce synthesis of the phage receptor in the host. The cells were collected by centrifugation and resuspended in one-half volume of 10 mM $MgSO_4$. Cells prepared in this manner were used for 1-2 days.

The phage were diluted serially in 10 mM MgSO$_4$, 10 mM Tris-HCl, pH 7.5, and 0.01% gelatin. Fifty μl of diluted phage were added to 0.2 ml of *E. coli* cells, and the mixture was incubated at 37° C. for 15 minutes to allow absorption of the phage. The infected cells were mixed with molten (47° C.) LB broth containing 0.7% agar and poured on an LB-agar plate. After the top agar hardened, the plates were incubated at 37° C. for 5–6 hours, at which time plaques could clearly be seen in the lawn of bacteria. Recombinant bacteriophages were distinguished from the vector by addition of Xgal (0.04%) and IPTG (0.4 mM) to the top agar. After 6–8 hours, nonrecombinant phages were blue while those carrying inserts were colorless.

Prior to further screening, the library of recombinant phages was amplified. Phages were diluted, mixed with *E. coli* Y1088, and plated as above at a density of about 10,000 phages/85 Mm petri plate. After about 6 hours of growth, the plates were transferred to 4° C. and 4 ml of 50 mM Tris-HCl, pH 7.5, 10 mM MgSO$_4$, 100 mM NaCl, 0.01% gelatin (SM) were added to the surface of the plates. The plates were rocked gently for 2 hours and the phage suspension was removed with a pipet. The combined phage suspensions were mixed with chloroform, the bacterial debris was removed by low-speed centrifugation and the phage library was stored in the presence of chloroform at 4° C.

EXAMPLE VIII

Identification of Recombinant Phages by Screening Lysogens

Recombinant bacteriophages were screened for their ability to produce a protein which is recognized by antibodies present in serum from chickens which have been infected with *E. tenella*. The phages were screened as lysogens, where they were grown as colonies and then induced for both phage and β-galactosidase production.

A 25 ml overnight culture of *E. coli* Y1089 (ΔlacU169 proA+ Δlon araD139 strA hflA [chr::Tn10] (pMC9)) (available from the American Type Culture Collection, accession number 37196) in LB +0.2% maltose was collected by centrifugation and the cells were resuspended in 12.5 ml of 10 mM MgSO$_4$. Phages from the amplified library described in Example VII were added to the cells at a multiplicity of infection of 2.5. The cells were incubated at 30° C. for 20 minutes and then plated on a cellulose acetate filter placed on an LB agar plate at a density of 5–10,000 colonies per 85 mm plate. The colonies were grown 8–12 hours at 30° C. To make a replicate filter, a nitrocellulose filter (premoistened with LB) was pressed on top of the colonies on the cellulose acetate filter, removed and placed colony-side up on a fresh LB agar plate, and stored at 4° C. The cellulose acetate filter with the remaining parts of colonies was placed on top of a nitrocellulose filter which was already in place on a fresh LB agar plate containing 0.4 mM IPTG. The lysogens were grown at 42° C. for another 2 hours to allow for induction of λ and of β-galactosidase. During this period, some cell lysis occurred and proteins were released, passed through the cellulose acetate filter, and bound to the nitrocellulose filter. After the induction period, the cellulose acetate filter was removed and the nitrocellulose filter was screened for the presence of antigens which were recognized by the anticoccidia antiserum.

The nitrocellulose filter was removed from the plate and washed (batchwise if more than one filter was being processed) with four 50 ml changes of Tris-buffered saline (TBS; 50 mM Tris-HCl, pH 8.0, 0.5M NaCl). The filters were then blocked with a solution of 3% gelatin in TBS. The filters could be blocked together if they were placed back-to-back. Ten ml of the blocking solution was used per 2 filters in an 85 mm petri dish. After 60 minutes, the blocking solution was removed and the primary antibody was added. The primary antibody consisted of 10 μl of chicken anticoccidia antiserum in 5 ml of 1% gelatin in TBS and 0.5 ml of normal rabbit serum. The primary antibody was allowed to react with the filters for 4 hours at room temperature with gentle rocking. After the incubation period, the filters were washed (also batchwise) with four 100 ml changes of TBS. The second antibody solution was then reacted with the filter to allow detection of the positive transformants. The second antibody solution consisted of 10 μl of rabbit antichicken IgG conjugated with horseradish peroxidase (available commercially). The second antibody was allowed to react with the filters for 1 hour at room temperature with gentle rocking. After the incubation, the filters were washed 4 times with 100 ml of TBS. The filters were then developed by placing them in the developing solution, which consisted of 32 mg of 4-chloro-1-naphthol, 12 ml methanol, 60 ml of TBS, and 120 μl of 30% H$_2$O$_2$. The developing solution was prepared freshly with components added in the order listed. The filters were left in the developing solution until color development was maximum (about 5 minutes). The filters were then washed with water, dried, and used to locate the positive colonies on the replicate nitrocellulose filter.

EXAMPLE IX

Identification of Recombinant Phages by Plague Screening

Phages from the amplified library of recombinant phages in Example VII were transfected into a host in which lysis and plaque formation occurs. The plaques were transferred to a nitrocellulose filter and were screened for their ability to bind to anticoccidia antibodies.

The host was *E. coli* Y1090 (ΔlacU169 proA+ Δlon araD139 strA supF [trpC::Tn10] (pMC9) (available from the American Type Culture Collection, accession number 37197), which was grown overnight in LB+0.2% maltose, centrifuged, and resuspended in 0.5 volume of 10 mM MgSO$_4$. Cells were used for 1–2 days. The amplified phage library was diluted in SM such that 50 μl contained 5–10,000 plaque-forming units. Fifty μl of the suitably diluted phage was added to 100 μl of the cell suspension. The mixture was incubated for 15 minutes at 37° C. to allow absorption of the phages. To the infected cells were added 2.5 ml of molten LB+0.7% agarose. The suspension was mixed briefly and plated on an LB-agar plate. After the top agarose had solidified, the plates were incubated at 42° C. for 5–6 hours. A nitrocellulose filter saturated with 0.01 M IPTG was laid over the plaques and the plate was incubated at 37° C. for 2 hours. The filter was removed, washed 4 times with 50 ml of TBS at room temperature, and incubated for at least 1 hour with gentle shaking at room temperature with 3% gelatin in TBS to reduce nonspecific binding of the antibodies. The blocking solution was removed and the primary antibody solution, consisting of 10 μl of chicken immune serum in 4.5 ml of 1% gelatin and 0.5 ml normal rabbit serum, was added. The filters were rocked gently in the primary antibody solution for at least 1 hour. The filter was then washed 4 times with 50 ml of TBS at room temperature and the second antibody solution, consisting of 10 ul of rabbit antichicken IgG conjugated with horseradish peroxidase in 5 ml of 1% gelatin in TBS, was added. The filter was rocked gently for 1 hour and then washed 4 times with 50 ml of TBS. The filters were developed by placing the filter in a freshly-prepared solution of 32 mg of 4-chloro-1-naphthol in 12 ml methanol, 60 ml of TBS, and 120 µl of 30% $H_2O_2$. After a short period of time, positive plaques turned dark blue and negative plaques were lighter blue or colorless.

An amplified library of recombinant bacteriophages consisting of 80,000 individuals was plated at a density of about 5000 plaques per plate. Screening with antiserum from infected chickens yielded one strongly positive (intense blue color) and several weakly positive (lighter blue) plaques. Areas on the original plates containing those plaques were picked into 1 ml of SM and the phages were plated again at different dilutions such that isolated plaques were obtained. Plates which had isolated plaques were screened as described above and the individual positive plaques were picked for analysis of the DNA and of the protein product made. The bacteriophage giving the strong positive response was designated λ5401 and was infected into *E. coli* Y1089 to produce a lysogen and the resulting strain was called GX5401. This strain has been deposited with the American Type Culture Collection Rockville, Md., and given accession number 53155.

EXAMPLE X

Isolation and Analysis of Bacteriophage λ DNA

Phage DNA was isolated from positive lysogens or plaques by procedures described by Maniatis, et al., supra. DNA was analyzed first by restriction enzyme analysis to determine the size of the insert in the vector.

For isolation from lysogens, colonies were picked from the duplicate filter and grown in LB at 30° C. That culture was used to inoculate 200 ml of LB+50 µg/ml ampicillin and the new culture was grown at 30° C. until it reached $A_{600}=0.5$. The culture then was shaken vigorously at 45° C. for 15 minutes and transferred to 37° C. for 2.5 hours. At this time, addition of chloroform caused rapid lysis of the culture. The cells were harvested by centrifugation for 10 minutes at 9,000 rpm in a Sorvall GS−3 rotor at 4° C. The cell pellet was resuspended in 5 ml of SM, a few drops of chloroform were added, and the mixture was vortexed. The mixture was left at room temperature for 30 minutes and then centrifuged for 20 minutes at 20,000 rpm in a Sorvall SS-34 rotor at 4° C. The supernatant solution was removed, pancreatic DNase and RNase were added to a final concentration of 1 jig/ml and the solution was incubated at 37° C. for 30 minutes. The phage particles then were collected by centrifugation at 28,000 rpm in a Beckmann 70.1 Ti rotor for 1 hour. The pellet was resuspended in 50 mM Tris-HCl, 5 mM EdTA, 0.1% SDS, pH 7.5, and heated at 68° C. for 30 minutes. The solution was extracted once with phenol, once with phenol:chloroform (1:1) and once with chloroform. The DNA in the aqueous phase was precipitated with ethanol.

For DNA isolation from plaques, phages were used to infect *E. coli* Y1088 and the infected cells were plated in 0.7% top agarose at a density of about 50,000 plaques per 150 mm petri plate. After 5-6 hours at 42° C. when nearly confluent lysis had occurred, 6.5 ml of SM were poured on the plates and they were incubated with gentle shaking at 4° C. for 2 hours. The phage suspension was removed from the plates, a few drops of chloroform were added, and the debris was removed by centrifugation for 10 minutes at 5,000 rpm in a Sorvall SS-34 rotor at 40° C.

The supernatant was removed and filtered through a 0.45µ filter. The phages in the filtrate then were collected by centrifugation through a discontinuous glycerol gradient. The glycerol gradients were prepared by placing 3 ml of 40% glycerol in SM in a polyallomer tube for a Beckman SW40 rotor and layering 3 ml of 5% glycerol in SM on top. The phage solution was layered carefully over the 5% glycerol layer and centrifuged for 1 hour at 35,000 rpm at 4° C. in an SW40 rotor. At the end of the run, the solutions were removed and the pelleted phages were resuspended in 0.5 ml of SM. Pancreatic RNase A was added to 10 µg/ml, pancreatic DNase I was added to 1 µg/ml, and the solution was incubated at 37° C. for 30 minutes. Following the incubation, 5 µl of 0.5M EdTA, pH 8.0 and 5 µl of 10% SDS were added and the solution was incubated at 68° C. for 15 minutes. The solution was extracted once with an equal volume of phenol, once with an equal volume of phenol:chloroform (1:1, v/v), and once with an equal volume of chloroform. The lambda DNA was precipitated by addition of an equal volume of isopropanol. The DNA was collected by centrifugation, washed once with 70% ethanol, dried, and resuspended in 10 mM Tris HCl, pH8, 0.1 mM EdTA. Typical yields from one 150 mm plate were 10-50 µg of DNA.

Digestion of the phage DNA isolated from GX5401 with EcoRI yielded two insert fragments, one having about 1800 base pairs and one having about 80 base pairs. The EcoRI fragments, or other fragments derived by digestion of the DNA with other restriction endonucleases, were subcloned into bacteriophage M13 for DNA sequence analysis by the method of Sanger, et al., supra. The DNA sequence is shown in FIG. 1.

EXAMPLE XI

Nuclear DNA Route

DNA is isolated from highly-purified *E. tenella* oocysts by the procedure of Blin and Stafford, *Nucleic Acids Res.*, 3, 2303-2308 (1976). Oocysts are suspended in 0.5M EdTA, 100 µg/ml proteinase K, and 0.5% Sarcosyl, and incubated at 50° C. for 3 hours. The solution containing lysed cell debris and high-molecular weight DNA is extracted 3 times with phenol, 3 times with sec-butanol to reduce the volume, and dialyzed exhaustively against 50 mM Tris-HCl, 10 mM EdTA, 10 mM NaCl, pH 8. The DNA is then treated with RNase at 100 µg/ml for 30 minutes at 37° C., extracted twice with phenol/chloroform (1:1), and dialyzed against 10 mM Tris-HCl, 1 mM EdTA pH 8.0.

The *E. tenella* DNA is incubated in 33 mM Tris-HCl, pH 7.6, 0.01M $MgCl_2$ at room temperature with DNase I (1 ng/10 µg of DNA, Boehringer Mannheim). After 10, 20, and 30 minutes, one-third of the reaction is transferred to a tube containing ⅛ volume of 0.1M EdTA, pH 8.0, to stop the reaction. Digested DNA is analyzed by electrophoresis on a 6% polyacrylamide gel. The fraction containing mostly DNA in the size range of 200-600 base pairs is run on a large, preparative gel, the region of the gel containing fragments of 200-600 base pairs is excised, and the DNA is electroeluted in 0.1×TBE. The DNA is concentrated and purified by use of an Elutip-d column (Schleicher and Schuell), used according to the manufacturer's instructions. The DNA is precipitated with ethanol.

The purified, concentrated DNA is collected by centrifugation, dried, resuspended in water, and prepared for insertion into λgt11 as described in Example V. The DNA which is methylated and modified by addition of EcoRl linkers is ligated into λgt11 and packaged as described in Example VI. Recombinant phages are screened as described in Examples VII and VIII.

EXAMPLE XII

Cloning of Gene-Length DNA Fragments Generated by Digestion of Genomic DNA with Mung Bean Nuclease In an alternative genomic DNA cloning method, gene-length fragments were generated by digestion of *E. tenella* DNA with mung bean nuclease using procedures described by McCutchan et al. (*Science*, 225, 625–628 1984)).

DNA isolated as described in Example XI was incubated in 0.2M NaCl, 1 mM ZnSO$_4$, 30 mM sodium acetate, pH 4.6, and various concentrations of formamide (30, 35, 40 and 45%) with 1 unit of mung bean nuclease (P-L Biochemicals) per μg of DNA. Incubations were done at 50° C. for 30 minutes. The DNA is analyzed by agarose gel electrophoresis and Southern blot analysis using a $^{32}$p-labeled fragment from Southern blot analysis using a $^{32}$p-labeled fragment from the positive phage described in Example IX as the probe. The reaction mixture which gives an indication of the presence of full-length gene fragments by hybridization is diluted four-fold with 10 mM Tris HCl, pH 8, 10 mM EDTA, extracted with phenol and ethanol precipitated.

The DNA was prepared for insertion into λgt11 by EcoRI methylation and addition of EcoRl linkers as described in Example V. The DNA was inserted into λgt11 and the recombinant phages are analyzed as described in Examples VI–IX.

EXAMPLE XIII

Transfer of DNA Sequences Encoding Coccidial Antigens to an Expression Plasmed Vector The β-galactosidase/coccidia antigen fusion gene identified in Example IX was transferred to a plasmid for production of that fusion gene product. GX5401 lambda DNA was digested with KpnI, extracted with phenol and ethanol precipitated. Plasmid pGX3213 (constructed by inserting the cloning bank from plasmid pUC18 (commercially available from Pharmacia P-L Biochemicals, and other sources) into the EcoRI-HindIII sites of pGX1066 [*E. coli* strain GX1186 (*E. coli* strain GX1170 transformed with pGX1066) has been deposited with the American Type Culture Collection, Rockville, Md., as ATCC 39955]) was digested with KpnI, extracted with phenol, and ethanol precipitated. The two KpnI-cut DNAs were ligated at about 100 μg/ml DNA concentrations using T4 DNA ligase, phenol extracted, and ethanol precipitated. The ligated DNA was digested with HindIII, diluted to about 1 μg/ml DNA concentration, and ligated with T4 DNA ligase. The ligation mixture was used to transform *E. coli* JM101 (ATCC 33876) which had been made competent for uptake of DNA by standard procedures. The transformants were screened for the presence of the β-galactosidase/coccidia antigen fusion gene by restriction digestion of plasmid DNA prepared by standard procedures. The plasmid carrying the coccidia antigen/β-galactosidase fusion gene was designated pGX3215. The plasmid is about 12 k.b. and carries the fusion gene and the *E. coli* lac operon regulatory elements such that synthesis of the fusion gene product is controlled by those regulatory elements. *E. coli* strain GX5408 (strain JM1OL transformed by pGX3215) has been deposited with the American Type Culture Collection Collection and given accession number 53154.

EXAMPLE XIV

Fermentation and Purification of the Coccidia Antigen/B-galactosidase Fusion Gene Product

*E. coli* strain GX5408 was grown overnight at 37° C. in 10 ml of LB broth containing 100 μg/ml ampicillin. One liter of LB broth containing 100 μg/ml ampicillin in a 2 liter flask was inoculated with the 10ml overnight culture and incubated with vigorous shaking at 37° C.. When the A$_{600}$ of the culture reached 0.6, 4 ml of 0.1M IPTG were added and incubation was continued for 2 hours.

After 2 hours, the cells were harvested by centrifugation at 4° C. at 7,000 rpm for 10 minutes in a Sorvall GS-3 rotor. The cell pellet (about 2–3 g wet weight per liter culture) was resuspended in 100 ml of 0.05M sodium phosphate, pH 7.0, and centrifuged again. The cells were resuspended in 0.05M sodium phosphate, pH 7.0 (5 ml/g wet weight of cells) and disrupted by sonication using a Branson Sonicator. Sonication was done for four 30-second bursts at full power with the cell suspension chilled in ice. The bursts were done at 1-minute intervals. Cell debris was removed from the sonicated suspension by centrifugation at 4° C. at 15,000 rpm for 20 minutes in a Sorvall SM-24 rotor. The supernatant was removed and the gene product was partially purified from it.

The following procedures were done at 4° C. Nucleic acids were removed from the extract by slow addition of 0.1 volume of 30% streptomycin sulfate (30% w/v in water) followed by centrifugation for 10 minutes at 10,000 rpm in a Sorvall SS-34 rotor. To the supernatant solution, crystalline ammonium sulfate was added slowly with stirring to a final concentration of 36% (0.21 g (NH$_4$)$_2$SO$_4$ per ml). The precipitated protein mixture containing the β-galactosidase/coccidia antigen fusion protein was collected by centrifugation at 10,000 rpm for 10 minutes in a Sorvall SS-34 rotor. The protein pellet was dissolved in 0.05 M Tris.HCl, pH 7.5.

The protein solution was applied to a column (1.5×50 cm) of Sephacryl 5-300 (Pharmacia) equilibrated in 0.05M Tris.HCl, pH 7.5. The protein was eluted with the same buffer. Column fractions were monitored for the presence of the β-galactosidase/coccidia antigen fusion protein by SDS-polyacrylamide gel electrophoresis. Fractions containing the fusion protein were pooled and the proteins were precipitated by adding ammonium sulfate to 36% as above. The protein was collected, dissolved in a minimum volume of 0.1M sodium phosphate, pH 7.5+0.2 mM dithiothreitol, and dialyzed extensively against the same buffer. SDS-polyacylamide gel electrophoresis demonstrated that the fusion protein has a molecular weight of 140,000–160,000 daltons of which 115,000 daltons is β-galactosidase and the remainder is coccidia antigen. The typical yield of fusion protein from 1 liter of culture was 10-20 mg of protein which contained 10-20% β-galactosidase/coccidia antigen fusion protein.

EXAMPLE XV

Testing the Effectiveness of the Antigenic Protein as a Vaccine

The antigenic protein purified in Example XIV was tested for ability to protect chickens against *E. tenella* infections by Harry Danforth and Pat Augustine of the Poultry Parasitic Diseases Lab, Animal Parasitology Institute of the USDA, Beltsville, Maryland. Birds previously unexposed to coccidial parasites were inoculated with purified antigen described in Example XIV. Groups of ten 4-week old birds were inoculated subcutaneously with 0, 600, 1200, 2400, and 4800 ng of antigen in Freunds' Complete Adjuvant. After three weeks, the birds were challenged with 75,000 *E. tenella* oocysts per bird in the drinking water. Six days after the challenge, the birds were evaluated for the severity of the infection. Parameters measured were weight gain, feed conversion, (amount of feed consumed/weight gain), and lesion scores (cecal pathology). The results of the test are shown in Table 1. In a similar experiment, birds which had been inoculated with 2400 μg of antigen were challenged with 75,000 oocysts and the same parameters as above were measured. The oocyst preparation used in this case was older and contained fewer viable organisms. Results of that experiment are shown in Table 2. The results based on all three parameters measured indicate that inoculation of chickens with the β-galactosidase/coccidia antigen fusion protein described here resulted in a decrease in the severity of coccidia infections.

TABLE 1

Effect of 5401 Protein Immunization with Heavy Eimeria Tenella Challenge (75,000 Oocysts/Bird)

| Treatment | Ave. Lesion Score | % Weight Gain | Feed Conversion |
| --- | --- | --- | --- |
| Controls-Not Challenged | 0 | 100 | 2.87 |
| Controls Challenged | 3.3 | 38 | 7.70 |
| 600 ng 5401 Challenged | 3.2 | 35 | 7.49 |
| 1200 ng 5401 Challenged | 2.5 | 62 | 4.42 |
| 2400 ng 5401 Challenged | 2.8 | 70 | 4.54 |
| 4800 ng 5401 Challenged | 2.5 | 48 | 4.28 |

TABLE 2

Effect of 5401 Protein Immunization with Light Eimeria Tenella Challenge

| Treatment | Ave. Lesion Score | % Weight Gain | Feed Conversion |
| --- | --- | --- | --- |
| Controls Not Challenged | 0 | 100 | 2.72 |
| Controls Challenged | 2.7 | 83 | 3.08 |
| 2400 ng 5401 Challenged | 1.4 | 93 | 2.69 |

EXAMPLE XVI

Expression of *E. tenella* Antigenic Protein on the Cell Surface of *E. coli*

For expression of the coccidia antigen on the surface of *E. coli*, it is produced as a fusion with the *E. coli* lamb protein, which is the maltose-binding protein located in the outer membrane. The lamB sequence is set forth in Clement and Hofnung, *Cell* 27:507 (1981). See also Benson and Silhavy, *Cell* 32:1325-1335 (1983).

The DNA fragment coding for the coccidia antigen is excised using EcoRI and purified away from the vector. The ends of the coccidia antigen DNA fragment are modified with EcoRI-XmaI adapter molecules so that the fragment can be inserted into the lamB gene which has been cut with XmaI. A plasmid pGX3216 carrying the lamB gene regulated by a hybrid $\lambda O_L P_R$ regulatory region is used. *E. coli* strain GX5409, which carries pGX3216, has been deposited with the American Type Culture Collection and given accession number ATCC 53158. Ligation of these fragments yields a hybrid lamB-coccidia antigen protein where the first 182 amino acids of the processed protein are lamB and the remaining amino acids are the coccidia antigenic protein. Because of the lamB sequences present at the amino-terminus, such hybrid proteins should be localized to the surface of the host cells.

EXAMPLE XVII

Testing the Effectiveness of *E. coli* Expressing Coccidia Antigens on the Surface as an Immunizing Agent

*E. coli* strains expressing the lamB-coccidia fusion on their surface are added ($10^2$ to $10^6$ cells/g feed) to a feed mixture for chickens. Birds are allowed to feed freely. Following one, two, or three weeks of feeding, birds are challenged with *E. tenella* oocysts in the feed, and are monitored for the development of the disease state. Birds are monitored for feed conversion, weight gain, and lesion scores for up to 6 weeks. Serum from the test birds are also monitored for production of antibodies against the antigen protein. Antigens which show protection are tested in a similar test protocol for protection against other species of coccidia.

EXAMPLE XVIII

Use of Synthetic Peptides Based on Coccidia Antigens as Vaccines

Synthetic peptides with an amino acid sequence of a portion of the coccidia antigen sequence (FIG. 1) are synthesized automatically using a commercial peptide synthesizer (Biosearch, Vega, Beckman). Any synthetic peptide may be potentially immunogenic. One which may be useful is a peptide homologous to the repeated regions found in the antigen (see FIG. 1). Others are chosen at random but selected for having a high content of hydrophilic residues and therefore likely to be exposed on the surface of the organism. Peptides are chosen to be longer than 6 amino acid residues. The peptide is coupled to an immunogenic carrier protein such as bovine serum albumin or hemocyanin using known techniques (Peters and Richards, *Am. Rev. Biochem*, 46:523-55 (1977)) and the resulting peptide/carrier protein is tested for in vivo activity as described in Example XV.

EXAMPLE XIX

Construction of Vaccinia Viruses That Express Avian Coccidia Antigen

The *E. tenella* genomic DNA lamBda phage clone banks described in Example XI and XII are screened by hybridization (Benton and Davis *Science* 186:180–182, 1977) with the 1800 base pair EcoRI fragments isolated from the lysogenic phage of GX5401 (see Example X) made radioactive by nick translation (Rigby, et al., *J. Mol. Biol.,* 113: 237, 1977).

Recombinant phage identified by hybridization are analyzed by restriction endonuclease mapping, Southern blotting (Southern, *J. Mol. Biol.:* 96: 503, 1975) and DNA sequencing (Sanger et al., supra) to identify the amino terminal codon of the antigen gene. The DNA sequence is also analyzed to make certain no introns are present in the coding sequence since there is no evidence that they would be processed by vaccinia virus. Using MRNA (see example II) the 5′ end of the gene can be confined using SI nuclease mapping (Berk and Sharp, *Cell,* 12: 721, 1977). At a location 15 to 20 base pairs 5′ to the amino terminal ATG of the coccidia antigen gene a SmaI site is inserted using oligonucleotide directed mutagenesis (Zoller and Smith, *Methods in Enzymology,* 100: 468–500, 1983). Likewise one of the same endonuclease sites is placed on the 3′ end of the gene several bases in the 3′ direction past the polyadenylation signal sequence (Wickens and Stephenson, *Science,* 226: 1045–1051, 1984) in the DNA. In the process of in vitro oligonucleotide directed mutagenesis to provide endonuclease sites, the coccidia antigen gene is also subcloned into phage M13 or a plasmid capable of single stranded replication. The restriction endonuclease sites added at the 5′ and 3′ ends of the gene are chosen based on their absence in the coccidia antigen gene and their presence at the appropriate site in the cotransfection plasmid, pGS20 in this case.

Plasmid pGS20, ATCC 39249 (Macket et al., *Journal of Virology,* 49: 857–864) which contains the vaccinia virus promoter for the 7.5K gene followed by BamHI and SmaI cloning sites all embedded within the vaccinia thymidine kinase gene, is digested with SmaI. The plasmid with the modified coccidia antigen gene is digested with the restriction enzyme specific for the inserted endonuclease sites and the antigen gene fragment is isolated. The fragment is then cloned into pGS20 at the BamHI or SmaI site 3′ to the 7.5K gene promoter in the proper orientation to be placed under its control. The result is a "coccidia transfection plasmid" that will insert the coccidia gene into the vaccinia TK gene through an appropriate in vivo recombination event.

The coccidia transfection plasmid (1 μg) and calf thymus carrier DNA (20 μg) is precipitated with calcium phosphate (Gram and Van der Eb, *Virology* 52: 456–457, 1973; Stone et al., *J. Virology,* 28: 182–192, 1978), then used to transfect TK-143 cells two hours after infection with wild type vaccinia virus strain WR at 0.01 to 0.05 PFU/cell. The virus infected, DNA cotransfected cells are allowed to grow for 2 days in Eagle's medium supplemented with 10% fetal bovine serum. The cell monolayer is then harvested in Eagle's medium with 2% fetal bovine serum, frozen and thawed 3X to release virus, then assayed for the presence of TK- recombinants (Weir et al., *Proc. Natl. Acad. Sci.,* 79: 1210–1214, 1982; Macket et al., supra) by infecting a monolayer of TK-143 cells with virus dilutions in the presence of 1% agarose in culture medium with 25 μg/ml bromodeoxyuridine (BrdUrd). In the presence of BrdUrd only TK- virus replicates. After three days, the monolayer of cells is stained with 0.005% of neutral red to identify live cells that take up the dye. Plaques of non-stained dead cells containing vaccinia virus are picked, the virus is replicated again under 25 μg/ml BrdUrd selective pressure, then assayed for the presence of coccidia DNA by hybridization (Macket et al., *Proc. Natl. Acad. Sci.,* 79: 7415–7419, 1982) and for the production of coccidia antigen by immunological techniques (Cremer et al., supra).

Vaccinia virus TK- recombinants positive for the expression of coccidia antigen are used to infect chickens intradermally. Two weeks later live coccidia challenge is given in the drinking water. Birds are analyzed for weight gain, lesion scores and feed conversion as described in Example XV.

EXAMPLE XX

Expression of Avian Coccidia Antigen in Yeast

To effect expression of the coccidia antigen by *Saccharomyces cerevisiae* gene fusion between yeast invertase and the antigen is constructed. The sequences controlling expression of the fusion protein encoded by this gene are derived from the invertase gene.

The invertase DNA sequence required in this invention exists in a plasmid designated YpGX610, which comprises the entire YEpl3 sequence (Broach. et al., *Gene* 8:121 (1979). The YEp13 plasmid is available from the American Type Culture Collection, ATCC catalog number 37115) and a segment of the invertase gene encoding the signal and mature protein through amino acid #103. The amino acid sequence of the invertase gene is given by Taussig and Carlson, *Nucleic Acid Research* 6:1943–1954 (1983). This plasmid has been identified as an invertase clone from a library of yeast DNA previously constructed.

Fusion of the genes encoding coccidia antigenic protein and invertase is accomplished by first adding appropriate restriction endonuclease recognition sites to the invertase and coccidia gene segments and ligating the DNA fragments to assemble the expression vector by standard techniques (Maniatis et al., supra). The invertase encoding region is excised from YpGX610 as an approximately 6.8 kb SalI fragment. SAII restriction endonuclease cleaves YpGX610 into two equal size fragments. These SalI fragments are ligated with M13mp8 (commercially available) which has been linearized with SalI restriction endonuclease. M13 cloning and transformation protocols have been described (Messing, *Meth. Enzymol.* 101:20–89 (1983). The cloned SalI invertase fragment can exist in M13mp8 in either of two orientations. The desired orientation for the invertase gene is clockwise. When single-stranded DNA is prepared from this recombinant M13 phage the sense strand of invertase DNA will be present. To identify M13 clones with invertase sequence in the proper orientation an oligonucleotide identical to a portion of the nonsense strand of this gene is util ized. For example, the oligonucleotide sequence GAA GTG GAC CAA AGG can be used to identify the desired clone by standard DNA hybridization protocols. The M13 clone containing invertase sequence is designated MGXI200. An oligonucleotide primer then is used to insert a BamHI restriction endonuclease recognition site near the end of the invertase sequence in MGX1200. The oligonucleotide 5′ ATT GAA AAA CCC ACT CGT GTG GAT CCT GTT GTA ATC AAC CAC is utilized for this purpose. Oligonucleotide directed mutagenesis and screening of plaques potentially containing the desired mutation are completed using standard protocols (Zoller and Smith, supra, 100 (1983)). Potential mutant clones are screened by hybridization with the same oligonucleotide used to prime the mutagenesis or by cutting double-stranded M13 DNA with BamHI restriction endonuclease. The desired clones have two recognition sites for BamHI. Correct alignment of the new restriction site is confirmed by DNA sequence analysis. The clone with an added BamHI site is designated MGX1201. The invertase sequence of MGX1201 is excised by cutting double-stranded MGX1201 with SalI and BamHI restriction endonuclease.

To alter the gene sequence encoding the coccidia antigenic protein by oligonucleotide directed mutagenesis the following protocol can be utilized. The gene encoding the coccidia antigen protein is excised from pGX3215 (Example XIII) as a 1.8 kb EcoRI fragment and is ligated with EcoRI linearized M13mp8. This EcoRI fragment can exist in two orientations in M13mp8. The desired orientation of the gene sequence is clockwise. Recombinant M13 plaques with the properly oriented gene are identified by DNA hybridization with the oligonucleotide 5' G C C C T C T T C T C C G. This M13 recombinant phage is designated MGX1202.

A recognition sequence for the enzyme BQIII is inserted by oligo-nucleotide directed mutagenesis at the start of the coccidia antigenic protein coding region. The oligonucleotide 5' CTCCGGTTTGGCCACAGATCTCAATTC-GTAATCATGG is used to prime the mutagenesis. Following transformation of E. coli with in vitro mutagenized MGX1202, plaques are screened either by identifying the new BqlII site by restriction endonuclease digestion or by hybridization screening with the mutagenic oligonucleotide. DNA sequence analysis is used to confirm insertion of the desired sequence. The new vector is designated MGX1203. The gene encoding the coccidia antigenic protein is excised from MGX1203 as a 1.8 kb BglII - HindIII restriction endonuclease fragment.

An expression vector containing the invertasecoccidia antigen fusion gene can be generated as follows. The MGX1201 vector is digested with SalI and BamHI and the fragment containing the invertase partial sequence excised in accordance with standard techniques. Similarly, MGX1203 is digested with BQIII and HindIII to excise the fragment carrying the coccidia antigen gene. A third DNA fragment, containing an origin of replication for yeast and at least one yeast selectable marker, also is needed. This fragment can be obtained, for example, from a vector designated YpGX1 (E. coli strain HB101 (YpGX1) has been deposited with the American Type Culture Collection, Rockville, Md. as ATCC 39692), which is the YEp13 vector with the yeast chromosomal SalI site removed. It contains a 2 micron (2μ) sequence and the chromosomal marker leu-2 and can be digested with SalI ind HindIII to excise a fragment of the vector which contains these two sequences.

The three fragments are ligated; since BamHI and BglII leave the same overhangs, the BglII end will anneal and ligate with the BamHI end. The desired vector, designated YpGX611, is properly identified by digestion with SalI and HindIII restriction endonuclease digests.

Various host strains carrying defects in the chromosomal LEU2 gene are transformed with YpGX611 by the protocol of Hinnen et al., *PNAS* 75:1929 (1978). The segment of the yeast 211 plasmid contained in YpGX611 permits autonomous replication of the vector in Saccharomyces, and the LEU2 gene complements the chromosomal defect. Only the transformed yeast cells will be able to grow in a medium lacking exogenous leucine. When sucrose is utilized as the sole carbon source, the invertase coccidia antigen gene will be fully induced. Expression of this gene is repressed when glucose is the carbon source.

Expression of the invertase - avian coccidia fusion protein is detected by Western bl ot analysis (Burnett, *Anal. Biochem.* 112:195-203 (1981)) using antibody specific for the coccidia antigenic protein. The cellular location of the fusion protein (cystoplasm or cell wall) is determined by Western blot analysis of fractionated cell extracts. Cytoplasmic location of the fusion protein allows production, isolation, and testing of the product as a "subunit"vaccine. Cell surface location of the fusion allows evaluation of the strain as a live vaccine.

EXAMPLE XXI

Identification of CDNA Clone Encoding Antigens GX3264, GX3271, and GX3273 with Chicken Immune Serum To identify additional *Eimeria tenella* sequences encoding antigens that bind anti-coccidial antibodies, new cDNA libraries were prepared using methods described in Example I-VII. The characteristics of these cDNA libraries are summarized in Table 3. cDNA library I, used to identify the GX5401 antigen, was prepared from a mixture of sporulated and unsporulated oocysts. In order to identify antigens that might be expressed at a particular state in Eimeria development, cDNA libraries III and IV were prepared starting with unsporulated or sporulated oocysts, respectively. These cDNA libraries were screened with the chicken immune serum originally used to identify the GX5401 antigen coding sequence and with a second chicken anticoccidial immune serum. The second serum, prepared at A.H. Robins Company, was obtained from chickens infected with six different species of Eimeria.

The new library screenings, conducted essentially as described in Example IX, resulted in the identification of clones encoding segments of the GX5401 antigen as well as two new antigens.

A clone encoding an antigen designated GX3264 was identified in cDNA library VIII by screening phage plaques with the same chicken immune serum used to identify GX5401. To determine the DNA sequence encoding the GX3264 antigen, the cDNA was transferred as an EcoRI fragment to bacteriophage M13. The DNA sequence encoding the GX3264 antigen, determined by the method of Sanger et al. is shown in FIG. 2. Comparison of the GX5401 and GX3264 coding sequences revealed that the GX3264 antigen is a fragment of the GX5401 antigen.

To generate a plasmid vector for expression of the GX3264 antigen, the methods used to assemble a plasmid vector for expression of GX5401 antigen were followed. The newly assembled plasmid (pGX3264) encodes the GX3264 antigen as part of a fusion protein with beta-galactosidase. E. coli strain JM101 was transformed with pGX3264 and induced with IPTG as described in Example XIV.

cDNA library VII was screened with the chicken immune serum obtained from A.H. Robins Company. Two phage plaques were identified that produce coccidial antigens reactive with this chicken immune serum. The coccidial DNA from these plaques was transferred to bacteriophage M13 for DNA sequence analysis by the method of Sanger et al. The antigens encoded by these cDNAs were designated GX3271 and GX3273. The DNA sequences encoding these two antigens are shown in FIGS. 3 and 4. The DNA sequences encoding the GX3271 and GX3273 antigens do not show homology with each other, nor with the GX5401 coding sequence. Plasmid expression vectors, analogous to pGX3264, were constructed for production of the GX3271 and GX3273 antigens in *E. coli*. These expression vectors were designated pGX3271 and pGX3273 and encode beta-galactosidase coccidial antigen fusion proteins.

TABLE 3

Clone Banks Constructed for *E. tenella* Antigen Screening

| Clone Bank | Cloning Vector | Source of DNA | Approximate Number of Clones |
| --- | --- | --- | --- |
| I | λgt11 | cDNA from unsporulated and sporulated oocysts | 80,000 |
| II | λgt11 | Mung bean nuclease-digested genomic DNA | 10,000 |
| III | λgt11 | cDNA from unsporulated oocysts | 15,000 |
| IV | λgt11 | cDNA from sporulated oocysts | 16,000 |
| V | λgt10 | cDNA from unsporulated oocysts | 500,000 |
| VI | λgt10 | cDNA from sporulated oocysts | 1,000,000 |
| VII | λgt11 | *E. tenella* fragments from 10% of library V | 50,000 |
| VIII | λgt11 | *E. tenella* fragments from 10% of library VI | 100,000 |

EXAMPLE XXII

Identification of Clones Encoding GS3262 and GS3276 with Monoclonal Antibodies

Several monoclonal antibodies (MCAs) that react with Eimeria proteins were obtained from Dr. Harry Danforth, U.S. Department of Agriculture, Beltsville, Maryland. These monoclonal antibodies were raised against proteins from the sprozoite stage of several species of Eimeria including *Eimeria tenella, Eimeria acervulina, Eimeria maxima,* and *Eimeria adenoeides*. Examples of these monoclonal antibodies and their characteristics are shown in Table 4. Immunofluorescence assays (IFA) were utilized by Dr. Danforth to identify the target site of these MCAs within the sporozoite.

To identify clones encoding coccidial antigens, cDNA library VII was screened with a mixture of monoclonal antibodies. Several phage plaques giving a positive reaction with the pooled MCAs were identified. Subsequent screenings of these positive plaques with individual MCAs resulted in the identification of plaques that react specifically with MCA 12-09. The monoclonal antibody was prepared against *Eimeria acervulina* and reacts with the refractile body in sporozoites of at least nine different Eimeria species. The monoclonal antibody inhibits the development of Eimeria in vitro. (Danforth, N.D., "Use of hybridoma antibodies combined with genetic engineering in the study of protozoan parasites: A review." In: *Research in Avian Coccidiosis.* McDougald et al., eds., *Proc. of the Georgia Coccidiosis Conference,* University of Georgia (1986).) DNA from the plaque with the largest cDNA insert was transferred to bacteriophage M13 for sequence analysis by the method of Sanger et al. The antigen encoded by this cDNA was designated GX3262. The DNA sequence and amino acid sequence for the GX3262 antigen is shown in FIG. 5. For expression in *E. coli,* a plasmid vector was assembled according to the protocol used for the GX5401 antigen (Example XIII). The expression plasmid, designated pGS3262, encodes a fusion protein composed of the first 1006 amino acids of beta-galactosidase followed by the GX3262 antigen.

The genomic DNA library prepared in Example XII was also screened with the pooled monoclonal antibodies. This library was prepared with mung bean nuclease treated *Eimeria tenella* DNA, and is cloned in λgtll. A clone which was initially identified with the pooled monoclonal antibodies was subsequently shown to produce an antigen which reacts specifically with monoclonal antibody 12-07. This monoclonal antibody was prepared against *Eimeria acervulina* and reacts with the sporozoite surface of at least nine different Eimeria species. The new antigen was designated GX3276. For DNA sequence analysis the cloned Eimeria DNA was transferred to M13 and the sequence was determined by the method of Sanger et al. The DNA sequence encoding the GX3276 antigen and the translation product is shown in FIG. 6.

For expression in *E. coli*, a plasmid expression vector was assembled according to the protocol established for the GX5401 antigen. The expression plasmid was designated GX3276. This plasmid encodes a fusion protein composed of the first 1006 amino acids of beta-galactosidase followed by the GX3276 antigen.

TABLE 4

Representative Monoclonal Antibodies Used for Antigen Screening

| MCA | Species Raised Against | IFA Binding Pattern | Species Specificity |
| --- | --- | --- | --- |
| B10 | *E. tenella* | surface & internal | *E. tenella* |
| D11 | *E. tenella* | tip of sporozoite | *E. tenella* |
| 12-07 | *E. acervulina* | surface | Cross-reactive |
| 12-09 | *E. acervulina* | refractile body | Cross-reactive all species |
| 41-13 | *E. maxima* | tip of sporozoite | Cross-reactive all species |
| 94-D2 | *E. adenoeides* | surface & internal | |
| D2 2c11 | *E. tenella* | surface | Specific |
| S16 P3E5 | *E. tenella* | surface & internal | Cross-reactive |

EXAMPLE XXIII

Hybridization Screening to Identify Extensions of GX3262 Antigen

The GX3262 antigen has a molecular weight of approximately 12,000 daltons. Western blot analysis of *Eimeria tenella* proteins previously revealed that the 12-09 MCA reacts with a coccidial protein of about 28,000 daltons. In order to identify clones encoding larger segments of the complete Eimeria protein, hybridization screening was employed.

The procedure used to screen recombinant phage libraries with specific oligonucleotide probes was adapted from Benton and Davis, Science 196:180 (1977). Packaged phage DNA from cDNA library VI was plated at a density of about 20,000–50,000 plaque forming units/plate on a 150 mm LB agar plate (plus 100 micrograms/ml ampicillin with *E. coli* strain Y1090). The plates were incubated overnight at 37° C. and were then chilled at 4° C. for one hour. Duplicate nitrocellulose filters were prepared by overlaying the plate for one minute with the first filter and then for three minutes with the second filter. The filters were placed in denaturing solution (1.5M NaCl, 0.5M NaOH) for two minutes and then were transferred to neutralizing solution ((2×SSC (0.03M sodium citrate, 0.3M NACl); 0.2M Tris.HCl (pH8.0)). The filters were rinsed in 2×SSC for two minutes and then placed between 3 MM paper and heated in vacuo for 1.5 hours at 80° C. to fix the DNA to the filter paper. The filters were prehybridized in 10× Denhardts, 6× SSC, 0.2% SDS at 60° C. for 2 hours. They were then hybridized at room temperature with a $^{32}$p labeled oligonucleotide with the sequence 5' GGGCGCGGAGTGCCTCT.

The filters were washed with 6× SSC at room temperature (by shaking in a beaker) for 30 minutes and were then washed with 6× SSC at room temperature for 15 minutes. Filters were exposed to Kodak XAR-2 film using two intensifying screens (Dupont Cronex Lightning Plus BH) for 3 hours. Plaques could clearly be seen. The filters were then washed with increasing stringency to identify positive plaques. The following washes in 6× SSC were performed.

a. 37.5° C. for 20 minutes
b. 50° C. for 15 minutes
c. 60° C. for 15 minutes

Positive plaques based on the 50° C. wash were picked and placed in one ml of SM (5.8 g NaCl, 29 MgSO$_4$·7H$_2$O, 50 ml 1M Tris.Cl (pH 7.5), 5 ml 2% gelatin). After about thirty minutes dilutions of the phage were made. Fifty microliters of each dilution was mixed with 100 microliters of Y1090 plating cells and incubated at 37° C. for 20 minutes. The cells were plated on LB in 3 ml top agarose (0.7%) and were then incubated overnight. One nitrocellulose filter was made from each plate. Hybridization with the oligonucleotide probe and filter washing was performed as previously described.

The filters were air dried and exposed to X-ray film with double screens at -80° C. for 4 hours. Several positive plaques were identified. Phage DNA from the positive plaques was prepared according to the method of Maniatis et al. (*Molecular Cloning: A Laboratory Manual*, Cold Spring Harbor Laboratory, New York (1982)) treated with restriction endonuclease EcoRI to excise the coccidial DNA fragment. The fragments were transferred to M13 for DNA sequence analysis. The DNA sequence for the largest clone, designated (GX3262ext4c) is shown in FIG. 7. This clone shows homology with the original GX3262 sequence and extends that sequence toward the N-terminal coding region. The GX3262 and GX3262(ext4c) coding sequences are compared in FIG. 8. The GX3262(ext4c) clone encodes a protein of about 27,000 daltons, close to the size of the coccidial protein reacting with the 12-09 monoclonal antibody.

EXAMPLE XXIV

Partial Purification of Beta-Galactosidase-GX5401 and Beta-Galactosidase-GX3264 Fusion Proteins from *E. coli*

*E. coli* strain GX1210 carrying the pGX5401 or pGX3264 plasmids was induced for expression of the coccidial antigen as described in Example VII. For purification of the coccidial antigens all steps were performed on ice or in a 4° C. cold room. The induced cells were resuspended in 50 mM Tris.HCl (pH 7.5) at a concentration of 1 gram cells (wet weight) per 5 ml buffer. The suspension was sonicated 4-5 times for 20 seconds each time in 20 ml batches to lyse the *E. coli* cells. The suspension became darker as the cells were lysed.

The cell lysate was centrifuged for 15 minutes at 15,000 rpm in a Sorvall SS-34 rotor. To the supernatant, 0.1 ml 30% (w/v) streptomycin sulfate was added dropwise. The suspension was stirred for ten minutes and then centrifuged for 10 minutes at 10,000 rpm in a Sorvall SS-34 rotor to remove precipitated nucleic acids.

To the supernatant 0.21 grams crystalline (NH$_4$)$_2$SO$_4$/ml was added slowly with stirring. This resulted in a 36 percent saturated solution, at which point the beta-galactosidase-GX5401 fusion protein precipitated. The protein was collected by centrifugation at 10,000 rpm in an SS34 rotor for 10 minutes. The pellet was re-dissolved in PBS buffer.

EXAMPLE XXV

Partial Purification of GX3262, GX3271, GX3273, and GX3276 Antigens Expressed in *E. coli* as Beta-Galactosidase Fusion Proteins The appropriate *E. coli* strain was induced for antigen production as described in Example VII. The cells were resuspended in 0.05M Tris.HCL (pH 7.5) at a concentration of one gram cells (wet weight) per ml buffer. The cells were lysed by sonication and the cell lysate was centrifuged at 15,000 rpm for 15 minutes in a Sorvall SS-34 rotor. The supernatant was discarded.

The pelleted material was resuspended in the same volume of 0.05M Tris-HCl (pH7.5) as used previously. The sonication and resuspension steps were repeated several times to remove most of the soluble protein from the final pellet. The pellet was then resuspended in 0.2 volume 6M guanidine HCl, 10 mM Tris-HCl (pH 7.5). The suspension was centrifuged for 10 minutes at 15,000 rpm in a Sorvall SS-34 rotor and then dialyzed against PBS. The fusion antigen precipitated as the guanidine HCl was removed. The pelleted material was washed several times with PBS and then resuspended in an appropriate volume of PBS.

EXAMPLE XXVI

Use of Partially Purified GX3262 and GX3264 Antigen to Reduce the Severity of *E. Tenella* Infections in Chickens To examine the ability of GX3262 and GX3264 antigens to provide protective immunity in one-day-old broilers (Hubbard×Hubbard) against an *E. tenella* infection, the following study was performed.

*E. coli* strains GX1210 (pGX3262) and GX1210 (pGX3264) were induced to synthesize the beta-galactosidase-coccidial antigen fusion proteins essentially as described in Example XIV. The beta-galactosidase GX3262 and beta-galactosidase GX3264 fusion proteins were partially purified following methods described in Examples XXV and XXIV, respectively. The partially purified proteins were suspended in phosphate buffered saline (PBS) and alhydrogel was added to a final concentration of 30%.

As summarized in Table 5, three treatment groups were set up. In the first group, broiler chickens were immunized subcutaneously on days 1, 7 and 21 with 100 μg of partially purified GX3262 antigen produced in *E. coli*. On day 28 the birds were challenged with *E. tenella* oocysts and lesion scores were determined on day 35.

Group 2 was treated in an identical manner, except that 100 μg doses of partially purified GX3264 antigen were used in the immunizations.

Group 3 was a control group that received only phosphate buffer saline on days 1, 7 and 21.

The results on this study are shown in FIG. 9. Treatment groups 1 and 2 both had average lesion scores that were dramatically reduced in comparison with Group 3. The average lesion score for the control group (Group 3) was 3.43, and for Groups 1 and 2 the average lesion scores were 1.56 and 1.98 respectively. The results of this study indicate that both the GX3262 and GX3264 antigens can significantly reduce the severity of *E. tenella* infections in broiler chickens.

TABLE 5

| Treatment Group | Day 1 2/3/87 | Day 7 2/9/87 | Day 14 2/16/87 | Day 21 2/23/87 | Day 28 3/2/87 | Day 35 3/9/87 |
|---|---|---|---|---|---|---|
| 1[c] | GX3262-03 100 μg in Alhydrogel | GX3262-03 100 μg in Alhydrogel | | GX3262-03 100 vg in Alhydrogel | +[a] | T[b] |
| 2[c] | GX3264-02 100 μg in Alhydrogel | GX3264-02 100 μg in Alhydrogel | | GX3264-02 100 μg in Alhydrogel | + | T |
| 3[d] | PBS | PBS | | PBS | + | T |

Chickens: 51 1-day-old Hubbard × Hubbard male chicks
Alhydrogel - 30%
All immunizations to be given subcutaneously in 0.1 mL.
[a]*E. tenella* oocyst challenge (to yield LS of 3)
[b]Termination
[c]n = 15
[d]n = 21

EXAMPLE XXVII

Use of Killed *E. coli* Cells Carrying the GX3262 Antigen to Reduce the Severity of *E. Tenella* Infection A study was performed to determine if killed *E. coli* cells carrying the GX3262 antigen can protect chickens against *E. tenella* infection. The *E. coli* strain GX1210 carrying plasmid pGX3262 was induced to express the GX3262 antigen as a beta-galactosidase fusion protein. After the induction, the cells were suspended in phosphate buffered saline and were killed by incubation at 65° C. for two hours. Alhydrogel was added to the killed cell suspension to a final concentration of 30 percent.

As outlined in Table 6, four study groups were set-up. In the first group, Hubbard × Hubbard chickens were immunized with 100 micrograms of beta-galactosidase-GX3262 fusion protein on day 7 and day 21 of age. Study groups 2 and 3 were treated similarly, except that these groups were immunized with 200 micrograms and 500 micrograms of beta-galactosidase GS3262 fusion protein on day 7 and day 21. The fourth group was a control that received only phosphate buffered saline on day 7 and day 21. Each group was challenged with *E. tenella* oocysts on day 28 and lesion scores were determined on day 34.

The results of this study are presented in Table 7. Each of the three groups immunized with the killed *E. coli* cells carrying the GX3262 antigen had lesion scores significantly reduced in comparison with the control group. This study showed that the GX3262 antigen can be administered in killed microbial cells and significantly reduce the severity of *E. tenella* infection.

TABLE 6

| Treatment Group | Immunizations(Day of Age) | | Infection Day 28 4/28/87 | Assay Day 34 5/4/87 |
|---|---|---|---|---|
| | Day 7 4/7/87 | Day 21 4/21/87 | | |
| 1[a] | 3262 *E. coli* 100 ug in Alhydrogel | 3262 *E. coli* 100 ug in Alhydrogel | +[c] | T[d] |
| 2[a] | 3262 *E. coli* 200 ug in Alhydrogel | 3262 *E. coli* 200 ug in Alhydrogel | * | T |
| 3[a] | 3262 *E. coli* 500 ug in Alhydrogel | 3262 *E. coli* 500 ug in Alhydroel | + | T |
| 4[b] | PBS | PBS | + | T |

Chickens: 75 7-day-old Hubbard × Hubbard Male Chicks. Weight and Select birds with 10% average weight - Randomize.
[a]n = 15
[b]n = 30
[c]*E. tenella* oocyts to result in lesion scores of 3.
[d]Termination. Lesion scores and weight gain to be determined.

All immunizations to be given subcutaneously in 0.2 mL volumes.

TABLE 7

Effect of Vaccination of One-Week-Old Broilers with Heat-Killed *E. coli* pGX3262

| Group | Treatment | Challenge[a] Day 28 | % Mortality Day 28 to Day 34 | | Lesion Score Day 34 X ± SD(n) |
|---|---|---|---|---|---|
| | | | Total | Coccidial | |
| 1 | 3262 *E. coli* 100 ug (2X) | + | 0 | 0 | 2.11 ± 1.14(14)[b] |
| 2 | 3262 *E. coli* 200 ug (2X) | + | 0 | 0 | 1.88 ± 1.16(14)[b] |
| 3 | 3262 *E. coli* 500 ug (2X) | + | 0 | 0 | 2.28 ± 1.11(15)[c] |
| 4 | PBS | + | 10.7 | 3.6 | 3.06 ± 0.78(26) |

[a]*E. tenella* oocysts - Lot #855B-81 - 42,000 oocysts/bird
[b]p < 0.01 as compared with PBS controls
[c]p < 0.05 as compared with PBS controls

EXAMPLE XXVIII

Examination of Cross-Species Protection by GX3262 and GX3264 Antigens in Live *E. coli* Cells A study was performed to determine if the GX3262 and GX3264 antigens can provide protection against infection by *Eimeria acervolina* as well as *Eimeria tenella*. The experimental protocol for this study is summarized in Table 8.

In this study, *E. coli* strain GX1210 transformed with pGX3262, pGX3264, or pGX3217, was induced with IPTG, and antigen production was monitored by SDS,polyacrylamide gel electrophoresis. Live *E. coli* cells were suspended in phosphate buffered saline and alhydrogen was added to a final concentration of 30%. The cells were injected subcutaneously into two-day-old broiler chickens. On day 24, the chickens were challenged with a mixture of *Eimeria tenella* and *Eimeria acervulina* oocysts. On day 29 the chickens were sacrificed, and cecal and duodenal lesion scores were monitored. Cecal lesions result primarily from the *E. tenella* infection, whereas duodenal lesions are the result of *E. acervulina* infection. The experimental results are summarized in Table 9. Control chickens were chal-

TABLE 8

| Group[a] | Immunization[d] Day 2 | Challenge[c] Day 24 | Assay Day 30 |
|---|---|---|---|
| 1<br>n = 15 + 3 | pGX3262 ($10^9$)<br>in 30% Alhydrogel | + | T |
| 2<br>n = 15 + 3 | pGX3262 ($10^8$)<br>in 30% Alhydrogel | + | T |
| 3<br>n = 15 + 3 | pGX3264 ($10^9$)<br>in 30% Alhydrogel | + | T |
| 4<br>n = 15 + 3 | pGX3264 ($10^8$)<br>in 30% Alhydrogel | + | T |
| 5<br>n = 15 + 3 | pGX3217[b]<br>in 30% Alhydrogel | + | T |
| 6<br>n = 34 + 8 | PBS | + | T |

[a]132 Starting -Culled at Day 10
[b]Control plasmid (carries no coccidial genes)
[c]*E. acervulina* and *E. tenella*
[d]All Live Recombinant *E. coli* vaccines

TABLE 9

Vaccination of 2-Day-Old Broilers with Live *E. Coli* pGX3262, pGX3264, or pGX3217 and Subsequent Protection Against *E. Acervulina* and *E. Tenella* Infection

| Group | Treatment Day 2 | Challenge[b] Day 24 | % Coccidial Mortality Day 24–29 | Lesion Score Cecal Day 29 | Lesion Score Duodenal Day 29 |
|---|---|---|---|---|---|
| 1 | *E. coli* pGX3262[a]($10^9$) Live in Alhydrogel | + | 20% | 2.78 ± 1.20 (15)* | 2.87 ± 1.13 (15)* |
| 2 | *E. coli* pGX3262[a]($10^8$) Live in Alhydrogel | + | 6.7% | 2.25 ± 1.32 (15)* | 2.13 ± 0.92 (15)* |
| 3 | *E. coli* pGX3264[a]($10^9$) Live in Alhydrogel | + | 7.7% | 2.77 ± 1.38 (13)* | 3.69 ± 0.85 (13) |
| 4 | *E. coli* pGX3264[a]($10^8$) Live in Alhydrogel | + | 14.3% | 2.39 ± 1.61 (14)* | 3.64 ± 0.93 (14) |
| 5 | *E. coli* pGX3217[a]($10^9$) Live in Alhydrogel | + | 13.3% | 4.00 ± 0 (15) | 3.80 ± 0.56 (15) |
| 6 | PBS | + | 18.2% | 3.98 ± 0.10 (33) | 3.85 ± 0.44 (33) |

[a]Induced with IPTG
[b]Challenged with a mixture of *E. acervulina* and *E. tenella*. 914,000 sporulated oocysts/bird
*$p < 0.01$ as compared with PBS controls lenged with the mixture of oocysts and treated subcutaneously with phosphate buffered saline (PBS). These chickens showed very severe infections and had cecal and duodenal lesion scores of 3.98 and 3.85 respectively.

A second group of chickens of chickens was treated with $10^9$ cells of *E. coli* strain GX1210 (pGX3217). These chickens were not protected against infection by either Eimeria species.

Two groups of chickens were treated at day 2 with either $10^8$ or $10^9$ cells of *E. coli* strain GX1210 (pGX3264). In this case, cecal lesion scores were significantly reduced but no significant reduction of duodenal lesions was observed. The results indicate that the 3264 antigen, which was originally identified in an *E. tenella* cDNA library screened with chicken immune serum against *E. tenella*, protects against *E. tenella* but not *E. acervulina*.

Two other groups of chickens (1 and 2) were treated at day 2 with either $10^9$ or $10^8$ cells of *E. coli* strain GX1210 (pGX3262). In both groups of chickens significant reduction of both cecal and duodenal lesion scores were observed. For example, in the group 2 chickens, the cecal and duodenal lesion scores were reduced to 2.25 and 2.13 respectively. These important experimental results show that an antigen encoded by a cDNA from *E. tenella* can significantly reduce the severity of both *E. tenella* and *E. acervulina* infections.

EXAMPLE XXIX

Expression of GX3262 Antigen in Yeast

For expression in the yeast *Saccharomyces cerevisiae*, the GX3262 antigen coding sequence was inserted into a vector analogous to YpGX283. The YpGX283 vector was fully described in the published PCT application PCT/US87/03048. The yeast expression vector encoding the GX3262 antigen (YpGX407) is shown in FIG. 10. In this vector, the GX3262 antigen coding sequence is linked to the yeast PH05 signal coding sequence by synthetic DNA. For expression of the coccidial antigen, yeast strain YGXD8 was transformed with YpGX407 by the protoplast method (Hinnen et al., *Proc. Natl. Acad. Sci., U.S.A.* 75:1929 (1978)). The transformed yeast strain was designated GX4100. The yeast cells were maintained on YNBD medium (0.7% yeast nitrogen base, 2% glucose. To express the coccidial antigen, the cells were transferred to a medium composed of 1% yeast extract, 2% bacto-peptone, 0.5% glucose, 2% galactose.

EXAMPLE XXX

Protection Against *E. tenella* Infection by a Yeast Strain Expressing the GX3262 Antigen To determine if yeast cells carrying the GX3262 antigen can provide protection against an *Eimeria tenella* infection, the following experiment was performed. Yeast strain GX4100 was induced for expression of the GX3262 antigen as described in Example XXIX. The cells were killed by formalin treatment and were then used to immunize broiler chickens (Hubbard×Hubbard). The cells were administered either subcutaneously or orally. Six different study groups were set up, with the protocol shown in Table 10.

In the first group, the chickens received 50 micrograms antigen subcutaneously on day 1 of age and then received subcutaneous boosts of 100 micrograms antigen on day 7 and day 14.

In the second group, the chickens received 50 micrograms of antigen subcutaneously on day 1 and then received 100 micrograms of antigen orally on days 7-14.

In the third group, the chickens only received antigen via the oral route on days 7-14.

In the fourth group, an oral dose of 100 micrograms antigen was administered orally on days 1-7.

In the fifth group, the chickens received 10 micrograms of antigen subcutaneously on day 1 an 100 micrograms on day 14.

The sixth group was a control that received only PBS on days 1, 7 and 14 via the subcutaneous route.

The results of this study, shown in Table 11, indicated that subcutaneous injection of the yeast cells carrying the GX3262 antigen resulted in reduction of lesions caused by Eimeria tenella, but that oral vaccination did not reduce the severity of infection. In groups 1 and 2 which received the killed yeast cells subcutaneously, the average lesion scores were 2.66 and 2.52, compared with 3.77 in the control group.

Group 5, which received 10 micrograms of antigen on day 1 and 100 micrograms on day 14 did not have a reduced lesion score level compared with the PBS control. It appears that the 10 microgram dose on day 1 may have been insufficient to generate an immune response.

The results of this study indicate that GX3262 antigen expressed in yeast can reduce the severity of Eimeria tenella infection in chickens.

TABLE 10

| | Immunization(Day of Age) | | | Infection Assay | |
|---|---|---|---|---|---|
| Group | Day 1 | Day 7 | Day 14 | Day 28 | Day 34 |
| 1 | GX4100[a] | GX4100 | GX4100 | +[b] | T[c] |
| n = 15 | 50 ug s.q. | 100 ug s.q. | 100 ug s.q. | | |
| 2 | GX4100 | GX4100 - oral | | + | T |
| n = 15 | 50 ug s.q. | 100 ug through Day 14 | | | |
| 3 | — | GX4100 - oral | | + | T |
| n = 15 | | 100 ug through Day 14 | | | |
| 4 | GX4100 - oral | — | — | + | T |
| n = 15 | 100 ug through Day 7 | | | | |
| 5 | GX4100 | — | GX4100 | + | T |
| n = 15 | 10 ug s.q. | | 100 ug s.q. | | |
| 6 | PBS | PBS | PBS | + | T |
| n = 30 | | | | | |

[a]GX4100 in formalin inactivated yeast expressing GX3262 recombinant E. tenella antigen
[b]E. tenella challenge
[c]Lesion score

TABLE 11

Effect of Oral or Subcutaneous Immunization of Day-Old Broilers with Formalin Inactivated Yeast Expressing GX3262

| Group | Treatment | % Mortality Total | % Mortality Coccidial | Live Chicks Day 34 | X ± SD[c] Lesion Score |
|---|---|---|---|---|---|
| 1[a] | 50 ug GX4100 1x s.q. 100 ug | 26.6%[c] | 6.6% | 10 | 2.66[d] ± 1.37 |
| 2[a] | GX4100 2x s.q. 50 ug GX4100 1x p.o. | 26.6% | 0 | 11 | 2.52[d] ± 1.35 |
| 3[a] | 100 ug GX4100 7x p.o. | 6.6% | 0 | 14 | 3.30 ± 1.10 |
| 4[a] | 100 ug GX4100 7x p.o. | 26.6% | 6.6% | 11 | 3.27 ± 0.91 |
| 5[a] | 10 ug GX4100 1x s.q. 100 ug GX4100 1x s.q. | 20.0% | 0 | 11 | 3.50 ± 0.50 |
| 6[b] | PBS .1 mL 3x s.q. | 30% | 6.6% | 21 | 3.77 ± 0.35 |

[a]n = 15
[b]n = 30
[c]32,000 oocysts/bird E. tenella 855-B88
[d]significant at p < 0.01 as compared to PBS controls

TABLE 12

| Group[a] | Immunization Day 2 | Challenge[d] Day 24 | Assay Day 30 |
|---|---|---|---|
| 1 n = 15 + 3 | GX3271-02[c] 50 ug in 30% Alhydrogel | + | T |
| 2 n = 15 + 3 | GX3271-02[c] 100 ug in 30% Alhydrogel | + | T |
| 3 n = 30 + 5 | PBS | + | T |

[a]107 starting - culled at 10 days
[b]Bacterin irradiated - Total exposure 580,000 rad; administered subcutaneously.
[c]Partially purified antigen - administered subcutaneously
[d]E. tenella sporulated oocysts to result in lesion score of 3-4
[e]Terminate

TABLE 13

| Group[a] | Treatment Day 2 | (n) | Challenge[d] Day 24 | % Coccidial Mortality Day 24-30 | Lesion Score X ± SD Day 30 |
|---|---|---|---|---|---|
| 1 | GX3271-02[c] 50 ug in 30% | (15) | + | 0 | 2.75 ± 1.31* |

TABLE 13-continued

| Group[a] | Treatment Day 2 | (n) | Challenge[d] Day 24 | % Coccidial Mortality Day 24-30 | Lesion Score X ± SD Day 30 |
|---|---|---|---|---|---|
| 2 | Alhydrogel GX3271-02[c] 100 ug in 30% Alhydrogel | (15) | + | 0 | 3.13 ± 0.69 |
| 3 | PBS | (30) | + | 3% | 3.53 ± 0.58 |

[a]107 starting - culled at day 24
[b]Bacterin irradiated - Total exposure 580,000 rad Subcutaneous administration of vaccine 0.2 mL
[c]Partially purified antigen administered subcutaneously
[d]E. tenella 855B105 42,000 sporulated oocysts/chicken
**p < 0.01 as compared to PBS controls
*p < 0.01 as compared to PBS controls

EXAMPLE XXXI

Use of Antigen 3271 to Protect Broiler Chickens Against E. tenella Infections

To determine if the GX3271 antigen can provide protection against *Eimeria tenella* infections, the following experiment was performed. *E. coli* strain GX1210 (pGX3271) was grown to an optical density (A600) of 0.5 and then induced with IPTG to synthesize the β-galactosidase-GX3271 fusion protein. The fusion protein was paritally purified as described in Example XV. The partially purified antigen was suspended in phosphate buffered saline and alhydrogel was added to a final concentration of 30%. The antigen was injected into one-day old broiler chickens (Hubbard × Hubbard).

As shown in Table 12, on Day 2 of age the Group 1 chickens were injected subcutaneously with 50 ug fusion antigen and group 2 was injected with 100 ug fusion antigen. The third Group was injected with phosphate buffered saline. On day 24 of age, the chickens were challenged with approximately 42,000 *E. tenella* oocysts and lesion scores were determined at day 30.

The results of the experiment are given in Table 13. The chickens in Group 3 had average lesion scores of 3.53. In the Group 2 chickens the lesions scores were reduced, but the difference was not statistically significant in comparison with the Group 3 chickens. In the Group 1 chickens, the average lesion score was 2.75, significantly different from the control chickens in group 3. These results indicate that partially purified 3271 antigen has the ability to reduce the severity of an *E. tenella* infection.

EXAMPLE XXXII

Use of GX3276 Antigen to Protect Broiler Chickens Against E. tenella Infections

A study was performed to determine if the GX3276 antigen can provide protection against *E. tenella* infection in broiler chickens (Hubbard × Hubbard). The GX3276 antigen was administered either as a partially purified antigen, or in heat-killed *E. coli* cells (bacterins). In each case the preparation was suspended in phosphate buffered saline and alhydrogel was added to a final concentration of 30%. The partially purified antigen was prepared as described in Example XXV.

As outlined in Table 14, the partially purified antigen was tested at two dose levels (25 and 50 micrograms) and the bacterins were tested at three dose levels (25, 100, and 200 micrograms). The birds were immunized subcutaneously on Day 7 and Day 21 of age and were challenged with 39,000 sporulated *E. tenella* oocysts on Day 28. Lesion scores were determined on Day 34.

The results for this study are shown in Table 15. In all cases, the average lesion scores obtained for immunized birds were reduced in comparison with birds receiving only phosphate buffered saline. For the bacterins, statistically significant reductions in lesion scores were observed in birds receiving two doses of either 25 ug or 200 ug of GX3276 antigen. In addition, the lesion scores were significantly reduced in birds receiving two doses of partially purified GX3276 antigen at the 50 ug level. The results indicate that the GX3276 antigen can reduce the severity of *E. tenella* infections in broiler chickens.

TABLE 14

| Group | Immunization(Day of Age) Day 7 9/8/87 | Day 21 9/22/87 | Infection Day 28 9/19/87 | Assay Day 34 10/5/87 |
|---|---|---|---|---|
| 1 n = 15 | 3276 E. coli[a] 25 ug in 30% Alhydrogel | 3276 E. coli 25 ug in 30% Alhydrogel | +[c] | T[d] |
| 2 n = 15 | 3276 E. coli[a] 100 ug in 30% Alhydrogel | 3276 E. coli 100 ug in 30% Alhydrogel | + | T |
| 3 n = 15 | 3276 E. coli[a] 200 ug in 30% Alhydrogel | 3276 E. coli 200 ug in 30% Alhydrogel | + | T |
| 4 n = 15 | GX3276[b] 25 ug in 30% Alhydrogel | GX3276 25 ug in 30% Alhydrogel | + | T |
| 5 n = 15 | GX3276[b] 50 ug in 30% Alhydrogel | GX3276 50 ug in 30% Alhydrogel | + | T |
| 6 n = 34 | PBS | PBS | + | T |

Chickens: 109 7-day-old broilers (Hubbard × Hubbard)
[a]Antigens given subcutaneously in 0.2 mL per chick. All antigens are heat-killed *E. coli* bacterins containing GX3276 antigen
[b]Antigens given subcutaneously. These antigens are purified *E. coli* lysates.
[c]Chickens challenge infected with *E. tenella* oocysts to obtain cecal lesions in the range of 3-4 for the PBS control chickens.
[d]Chickens terminated day 6 post challenge and lesion scored.

TABLE 15

Effect of Vaccination of One-Week-Old Broilers with Either GX3276-02 or Heat-killed E. coli pGX3276 Study 90761

| Group | Treatment | Challenge Day 28 | % Coccidial Mortality | Lesion Score Day 34 X ± SD (n) |
|---|---|---|---|---|
| 1 | 3276 E. coli[a] 25 ug (2X) | +[c] | 0 | 2.41 ± 1.31(14)** |
| 2 | 3276 E. coli[a] 100 ug (2X) | + | 0 | 2.88 ± 1.20(14) |
| 3 | 3276 E. coli[a] 200 ug (2X) | + | 0 | 2.46 ± 1.48(14)** |
| 4 | GX3276-02[b] 25 ug (2X) | + | 0 | 3.15 ± 1.10(15) |
| 5 | GX3276-02[b] 50 ug (2X) | + | 0 | 2.72 ± 1.03(13)* |
| 6 | PBS | + | 3.2% | 3.54 ± 0.53(29) |

[a]Heat-killed *E. coli* pGX3276 #1
[b]GX3276-02, partially purified, was 5% of total protein.
[c]Chickens were challenged with *E. tenella* oocysts - Batch #855B-94 - 39,000 sporulated oocysts per bird (oocysts were chloroxed prior to challenging the birds)
*p < 0.05 as compared with PBS controls
**p < 0.01 as compared with PBS controls

EXAMPLE XXXIII

Use of the Hybrid Phage Lambda Promoter OL/PR to Direct Expression of the GX3262 Antigen in *E. coli*

A new expression vector encoding the beta-galactosidase-GX3262 fusion protein was assembled. In this vector, designated pGX5305, expression of the fusion protein is directed to a hybrid phage lamBda promoter designated OL/PR. This hybrid promoter was fully described in European Patent Application No. 85903899-4. The promoter is especially useful because induction is based on a thermal shift, rather than a chemical such as IPTG.

Figure 11:
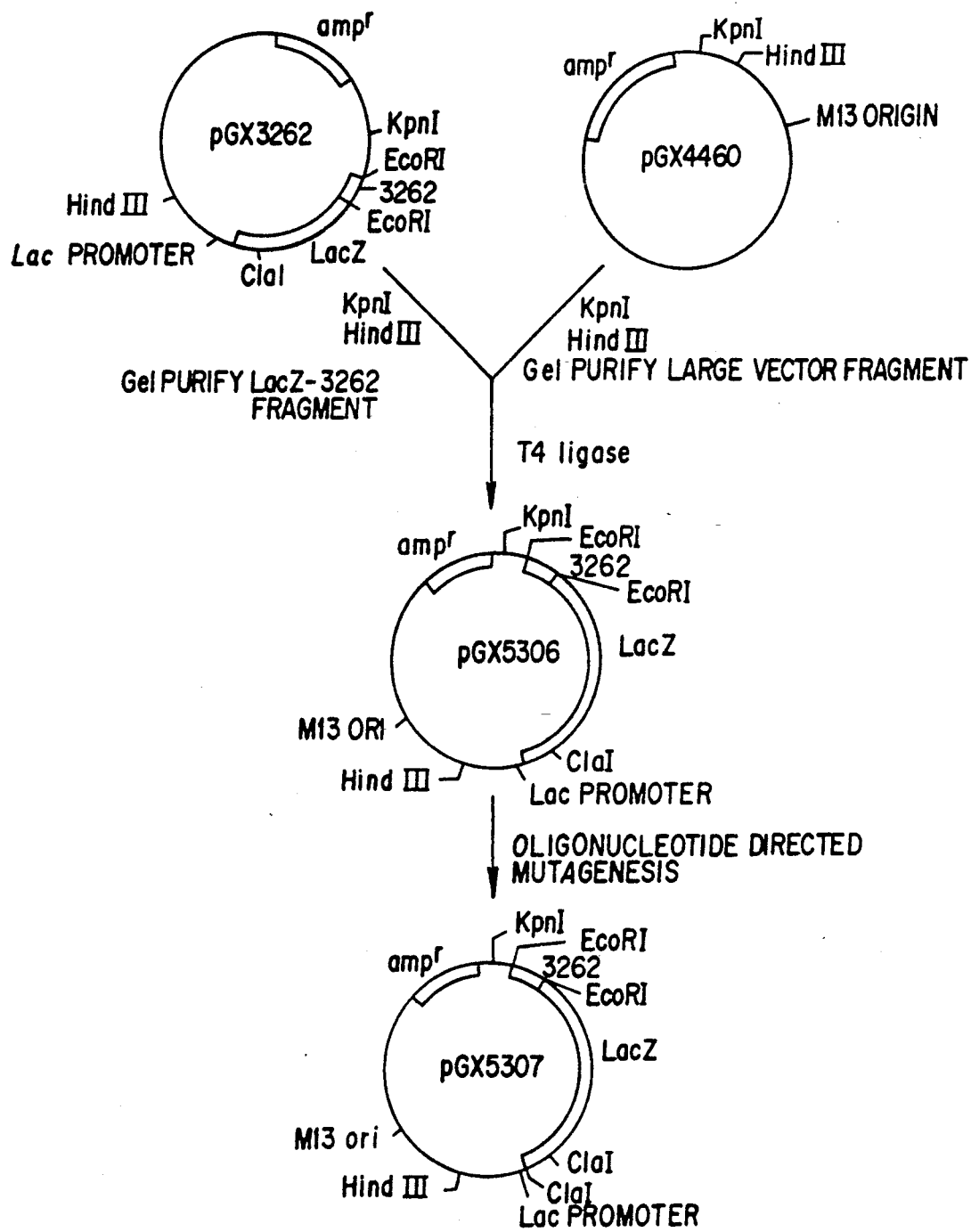
FIG. 11 shows the construction of plasmid pGX5307.
Figure 12:
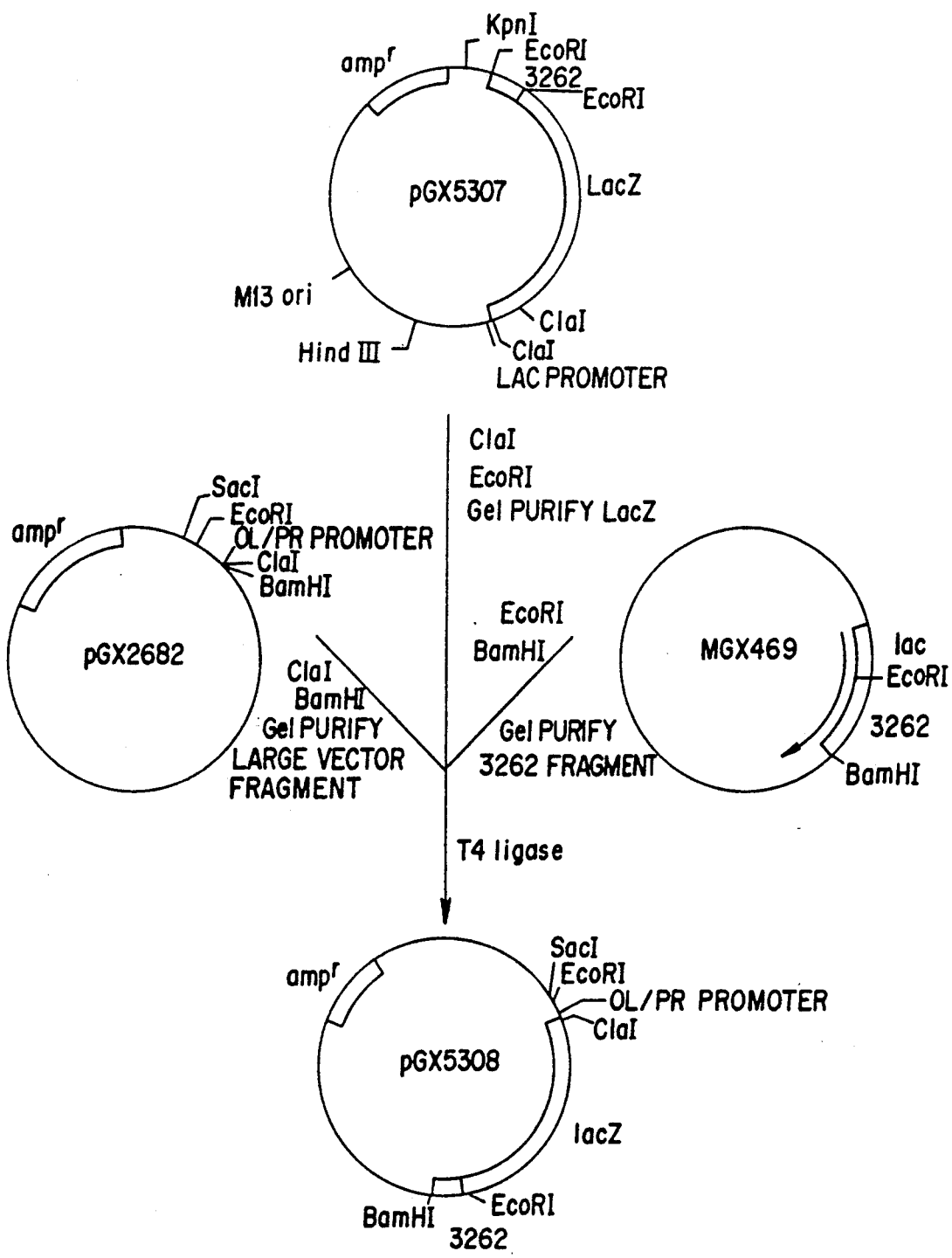
FIG. 12 shows the construction of plasmid pGX5308.
Figure 13:
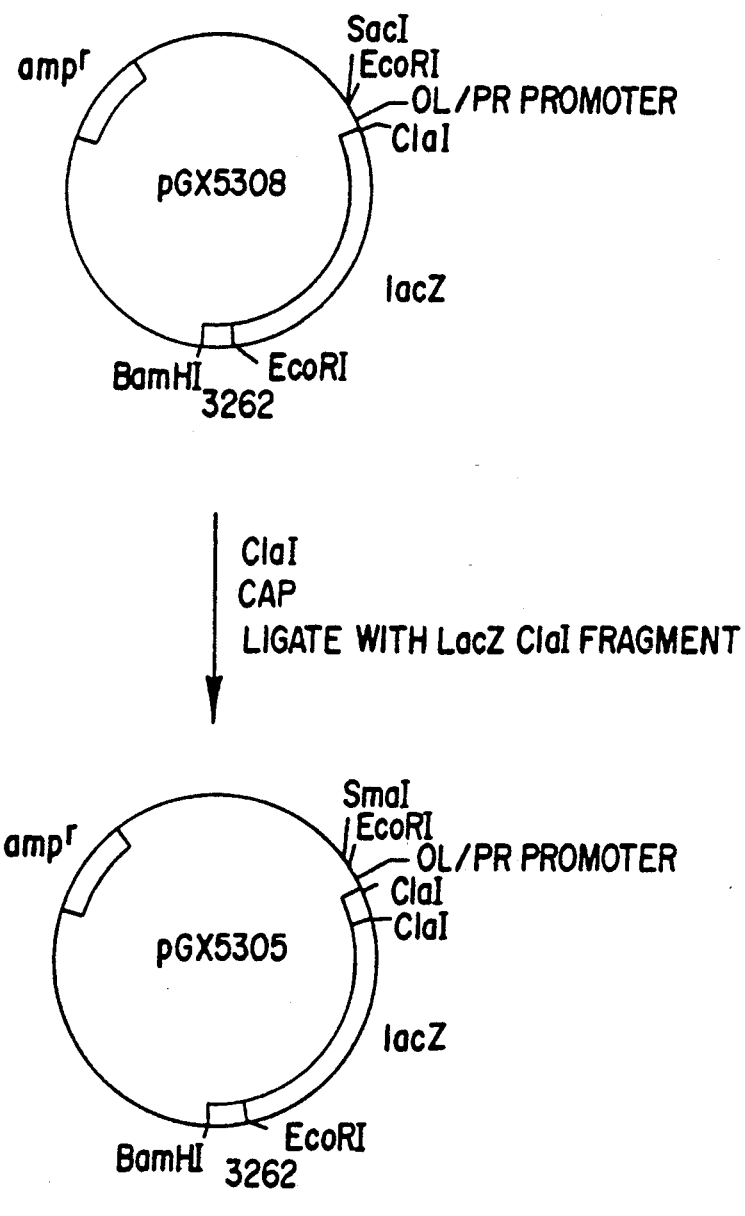
FIG. 13 shows the construction of expression vector pGX5305.

To assemble pGX5305, the following procedure was utilized. The procedure is depicted in FIGS. 11-13. First, the lac promoter and beta-galactosidase-GX3262 coding sequence was excised from pGX3262 with restriction endonuclease KpnI and HindIII and ligated with a fragment of pGX4460 also generated with KpnI and HindIII restriction endonucleases. The newly assembled vector, pGX5306, carried the lac promoter linked to the beta-galactosidase-GX3262 coding sequence but differed from pGX3262 because it also carried the replication origin from bacteriophage M13. Therefore, single-stranded pGX5306 DNA could be prepared and used as a template for oligonucleotide-directed mutagenesis. This technique was used to insert a ClaI restriction site at the start of the beta-galactosidase-GX3262 coding sequence. The ClaI site was useful for separating the beta-galactosidase coding sequence from the lac promoter. An oligonucleotide with the sequence 5' CATGGTCATCGATGTTTCCTG was used to prime the mutagenesis. Plasmid pGX5307 carried the new ClaI site which was first detected with ClaI enzyme and confirmed by DNA sequence analysis. The next step in the assembly was complicated by the presence of a natural ClaI site in the beta-galactosidase coding sequence. Therefore, another intermediate vector, pGX5308, was assembled (FIG. 12). Plasmid pGX5307 was digested with restriction endonucleases ClaI and EcoRI and the beta-galactosidase coding sequence was gel-purified. This fragment lacked the ClaI fragment encoding the N-terminus of beta-galactosidase in pGX5307. Next, the ClaI/EcoRI fragment was used in a three-way ligation that resulted in the assembly of pGX5308. In the three-way ligation, the ClaI/EcoRI fusion protein coding segment from pGX5307 was linked with the EcoRI/BamHI GX3262 coding sequence from MGX469 so that a ClaI/BamHI fragment was formed. These fragments were joined with a ClaI/BamHI fragment of pGX2682 to generate plasmid pGX5308. The N-terminal beta-galatosidase coding sequence was then excised from pgX5307 with endonuclease ClaI and ligated with pGX5308 which was linearized with ClaI and treated with calf alkaline phosphatase, thereby generating expression vector pGX5305 (FIG. 13). *E. coli* strain GX1201 which carries the gene for the temperature sensitive phage lambda repressor cI857 was transformed with pGX5305.

EXAMPLE XXXIV

Use of Strain GX1201 (pGX5305) to Reduce the Severity of an *E. tenella* Infection

*E. coli* strain GX1201 (pGX5305) was grown in LB media plus 100 micrograms/ml ampicillin at 30° C. to an $A_{600}$ of 0.5 and then shifted to 41° C. to induce expression of the beta-galactosidase-GX3262 fusion protein. In addition, strain GX1210 (pGX3262) was induced for expression of the beta-galactosidase-GX3262 fusion protein with IPTG. The live *E. coli* cells were then used in the following study.

Two-day-old Hubbard×Hubbard chickens were injected subcutaneously with 1×109 live cells of either GX1201 (pGX5305) (Group 1) or GX1210 (pGX3262) (Group 2). A control group was inoculated with phosphate buffered saline on day two. The chickens were challenged with 37,000 *E. tenella* sporulated oocysts/bird on Day 23 and lesion scores were determined on Day 29. The results of the study are shown in Table 16. The control group had an average lesion score of 3.13. The chickens in Groups 1 and 2 had average lesion scores of 1.33 and 2.30, significantly reduced in comparison with the control group. The results show that *E. coli* strains in which GX3262 antigen expression is regulated by the lac promoter or the OL/PR promoter can reduce the severity of an *E. tenella* infection in broiler chickens.

TABLE 16

| Group | Treatment Day 2 | Challenge[c] Day 23 | % Coccidial Mortality Day 23–29 | Lesion Score Day 29 |
|---|---|---|---|---|
| 1 | *E. coli* GX1201 (pGX5305)[a] live in alhydrogel | + | 0 | 1.33 ± 1.15 (12)** |
| 2 | *E. coli* pGX3262[b] live in alhydrogel | + | 0 | 2.30 ± 1.44 (14)* |
| 3 | PBS | + | 0 | 3.13 ± 0.87 (38) |

[a]Induced by 30–41° C. shift.
[b]Induced with IPTG.
[c]Challenge with E. tenella, Batch 855B-105, 37,000 sporulated oocysts/bird.
*p < 0.05 as compared with PBS controls.
**p < 0.01 as compared with PBS controls.

While certain representative embodiments and details have been shown for the purpose of illustrating the invention, it will be apparent to those skilled in the art that various changes and modifications may be made therein without departing from the scope of the invention.

I claim:

1. A clones gene comprising the deoxyribonucleotide sequence, and the amino acid sequence encoded thereby, of GX3262 as shown in FIG. 5 wherein said amino acid sequence is capable of eliciting a protective immune response against *E. tenella* and *E. acervulina* when administered to an avian host.

2. An expression vector comprising the cloned gene in claim 1 under the control of a regulatory region capable of directing the expression of said deoxyribonucleotide (DNA) sequence.

3. The expression vector of claim 2 wherein the vector is selected from the group consisting of plasmids, bacteriophages, or viruses.

4. A host organism transformed by the expression vector of claim 2 selected from the group consisting of gram positive bacteria, gram negative bacteria, yeast, fungi, and mammalian cells.

5. A host organism transformed by the expression vector of claim 2 wherein said host is *E. coli*.

6. A host organism transformed by the expression vector of claim 2 wherein said host is *Saccharomyces cerevisiae*.

* * * * *